United States Patent
Turk et al.

(10) Patent No.: US 11,410,747 B2
(45) Date of Patent: Aug. 9, 2022

(54) ESTIMATING PRE-PCR FRAGMENT NUMBERS FROM POST-PCR FREQUENCIES OF UNIQUE MOLECULAR IDENTIFIERS

(71) Applicant: LEXOGEN GMBH, Vienna (AT)

(72) Inventors: Andreas Turk, Vienna (AT); Michael Moldaschl, Vienna (AT)

(73) Assignee: LEXOGEN GMBH, Vienna (AT)

(*) Notice: Subject to any disclaimer, the term of this patent is extended or adjusted under 35 U.S.C. 154(b) by 270 days.

(21) Appl. No.: 16/649,591

(22) PCT Filed: Sep. 21, 2018

(86) PCT No.: PCT/EP2018/075606
§ 371 (c)(1),
(2) Date: Mar. 20, 2020

(87) PCT Pub. No.: WO2019/057895
PCT Pub. Date: Mar. 28, 2019

(65) Prior Publication Data
US 2020/0279613 A1 Sep. 3, 2020

(30) Foreign Application Priority Data
Sep. 22, 2017 (EP) .................................. 17192640

(51) Int. Cl.
*C12Q 1/68* (2018.01)
*G16B 20/10* (2019.01)
(Continued)

(52) U.S. Cl.
CPC ............. *G16B 20/10* (2019.02); *C12Q 1/686* (2013.01); *C12Q 1/6851* (2013.01); *G16B 5/00* (2019.02)

(58) Field of Classification Search
CPC ........................................................ C12Q 1/68
(Continued)

(56) References Cited

U.S. PATENT DOCUMENTS

2016/0026758 A1 1/2016 Jabara et al.
2018/0355416 A1* 12/2018 Mischel ............. C12Q 1/6886

FOREIGN PATENT DOCUMENTS

EP          2 868 752 A1    5/2015
WO     2012/148477 A1   11/2012
(Continued)

OTHER PUBLICATIONS

International Search Report and Written Opinion relating to International Application No. PCT/EP2018/075606, dated Oct. 18, 2018; 18 pgs.
(Continued)

*Primary Examiner* — Aaron A Priest
(74) *Attorney, Agent, or Firm* — Polsinelli PC; Tara A. Nealey

(57) ABSTRACT

The invention relates to a method of estimating a nucleic acid copy number after amplification comprising the steps of providing a sample comprising nucleic acids of a to be determined number of copies; attaching variable labels to said nucleic acids; amplifying said nucleic acids with the labels with a nucleic acid duplication procedure, preferably PCR; determining amounts of amplified nucleic acid copies with a label, each amount is determined for nucleic acid copies with a different label; and providing an estimation of the nucleic acid copy number in the sample based on the determined amounts of amplified nucleic acid copies; as well as computer program products adapted for performing such methods.

15 Claims, 13 Drawing Sheets

(51) Int. Cl.
  *G16B 5/00* (2019.01)
  *C12Q 1/6851* (2018.01)
  *C12Q 1/686* (2018.01)
(58) Field of Classification Search
  USPC .......................................................... 435/6
  See application file for complete search history.

(56) References Cited

FOREIGN PATENT DOCUMENTS

| WO | 2017/051387 A1 | 3/2017 |
| WO | 2017/205691 A1 | 11/2017 |
| WO | 2019/057895 A1 | 3/2019 |

OTHER PUBLICATIONS

Fu et al., "Counting individual DNA molecules by the stochastic attachment of diverse labels," PNAS, 2011, pp. 9026-9031, vol. 108, No. 22.

Fu et al., "Molecular indexing enables quantitative targeted RNA sequencing and reveals poor efficiencies in standard library preparations," PNAS, 2014, pp. 1891-1896, vol. 111, No. 5.

Roberts et al., "Improving RNA-Seq expression estimates by correcting for fragment bias," Genome Biology, 2011, R22, pp. 1-14, vol. 12, No. 3.

Tuerk et al., "Mixture models reveal multiple positional bias types in RNA-Seq data and lead to accurate transcript concentration estimates," PLOS Computational Biology, 2017, e1005515, pp. 1-16, vol. 13, No. 5.

\* cited by examiner

ESTIMATING PRE-PCR FRAGMENT NUMBERS FROM POST-PCR FREQUENCIES OF UNIQUE MOLECULAR IDENTIFIERS

CROSS-REFERENCE TO RELATED APPLICATIONS

This application is a U.S. National Stacie Application of International Application No. PCT/EP2018/075606, filed Sep. 21, 2018, which claims priority from EP Patent Application No. 17192640, filed Sep. 22, 2017, the entire contents of which are hereby incorporated by reference in their entirety.

The invention relates to a method of estimating a nucleic acid copy number after amplification comprising the steps of providing a sample comprising nucleic acids of a to be determined number of copies; attaching variable labels to said nucleic acids; amplifying said nucleic acids with the labels with a nucleic acid duplication procedure, preferably PCR; determining amounts of amplified nucleic acid copies with a label, each amount is determined for nucleic acid copies with a different label; and providing an estimation of the nucleic acid copy number in the sample based on the determined amounts of amplified nucleic acid copies; as well as computer program products adapted for performing such methods.

FIELD OF THE INVENTION

The present invention relates to the field of correcting biased nucleic acid amount determination methods, wherein said bias is introduced by amplification methods.

BACKGROUND OF THE INVENTION

Figure 1:
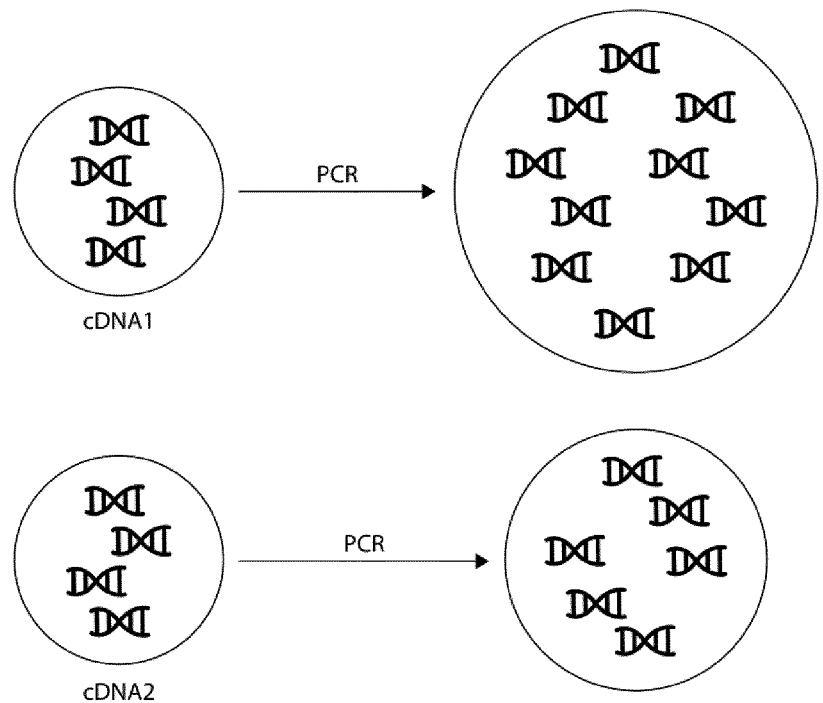

Polymerase chain reaction (PCR) amplifies nucleic acids by applying multiple cycles of denaturation, annealing and polymerization. Since the efficiency of each step depends on the input sequence, PCR amplification can introduce a sequence specific bias, meaning that different nucleic acids with different sequences will be amplified by different ratios. For RNA-Seq (RNA sequencing, in particular fragment or shotgun sequencing), for instance, this can lead to inaccurate gene and isoform quantification (FIG. 1).

WO 2017/051387 A1 relates to a method of determining complexity of a nucleic acid sample using codewords and by observing a codeword entropy.

Figure 2:
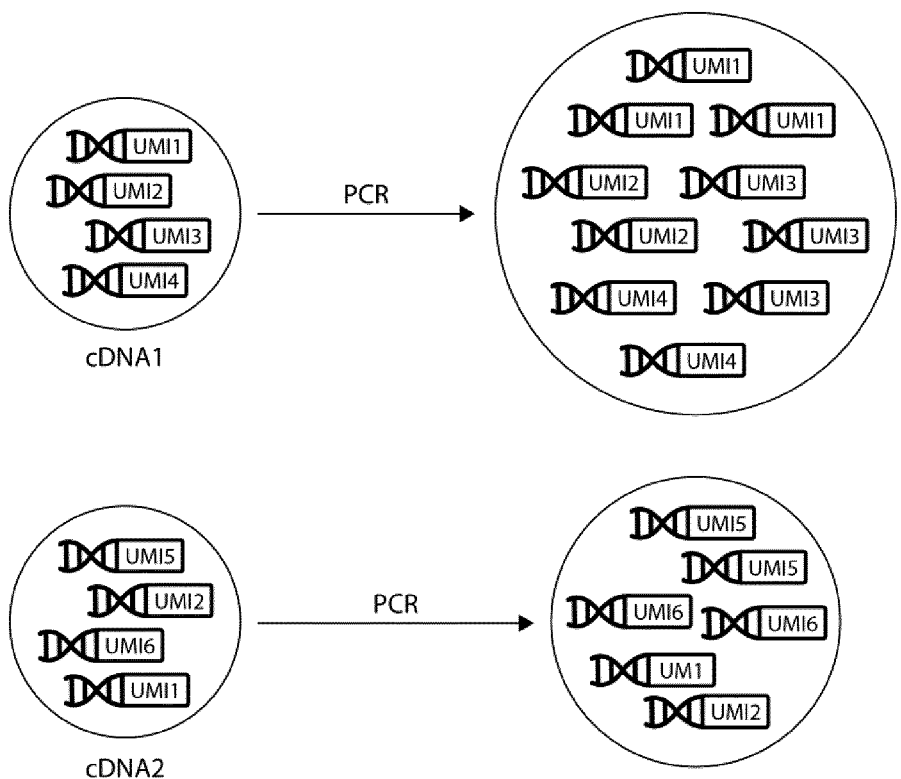
Figure 3:
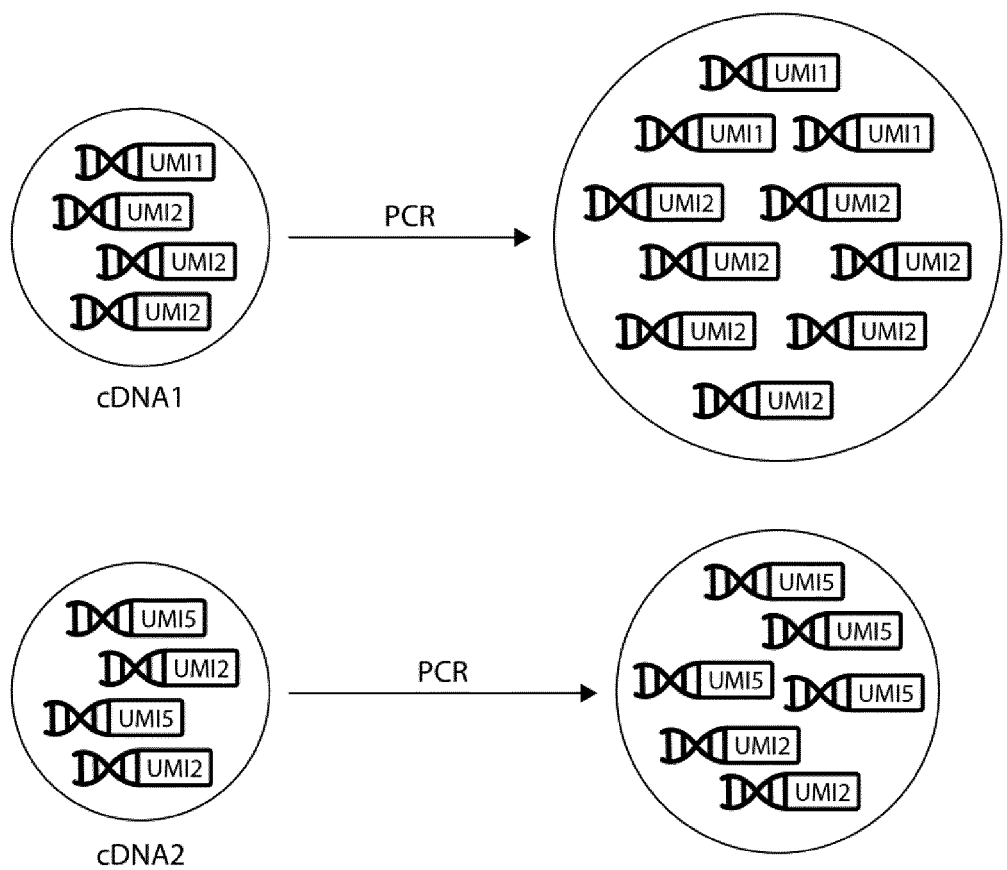

Labels, like unique molecular identifiers (UMIs), also called molecular barcodes, have been developed to identify PCR duplicates and reduce the effects of sequence specific PCR bias. UMIs are oligonucleotides with, mostly, random nucleotide distribution at each position which are ligated to DNA fragments prior to PCR amplification. If UMIs are evenly distributed and their number is considerably larger than a pool of identical fragments, then it is unlikely that the same UMI is ligated to two different fragments in the pool. In this case, the number of distinct UMIs in the pool after PCR is the same as the number of its fragments before PCR. Hence, variations in PCR efficiency for different pools can be corrected by counting the number of distinct UMIs rather than the number of fragments in each pool after PCR (FIG. 2). However, this simple counting routine becomes inaccurate if UMIs are not evenly distributed, for instance, due to ligation bias or uneven nucleotide insertion in UMI generation or distribution at positions within the UMI oligonucleotide. An uneven UMI distribution has the same effect as an insufficient size of the UMI set. In both cases, the same UMI will be ligated with high probability to two fragments leading to an underestimate of the pre-PCR number of fragment copies (FIG. 3).

Accordingly, there is a need for improved methods, that are able to estimate an amount of nucleic acids based on measuremens of amounts after an amplification and correct such amplification biases.

SUMMARY OF THE INVENTION

The present invention provides a method of estimating a nucleic acid copy number in a sample (using estimations after an amplification) comprising the steps of
a) providing a sample comprising nucleic acids of a to be determined number of copies;
b) attaching variable labels to said nucleic acids;
c) amplifying said nucleic acids with the labels with a nucleic acid duplication procedure;
d) determining amounts of amplified nucleic acid copies with a label, each amount is determined for nucleic acid copies with a different label; and
e) providing an estimation of the nucleic acid copy number in the sample of step a) based on the determined amounts of step d) by
approximating a probability of the labels of attaching to a nucleic acid by for at least two, preferably at least four, at least ten or more, different nucleic acid species in the sample: averaging the amounts of said label for different nucleic acid species after amplification; and iteratively or stepwise (A)

refining an expected number of nucleic acid copies in the sample based on the number of distinct detected labels in step d) and the expectation of the number of different labels to attach to a nucleic acid according to the probability of the labels of attaching to a nucleic acid copy and a previous iteration or pre-set value of an expected number of nucleic acid copies in the sample or an estimated amplification efficiency;
or (B)

(i) modelling probability distributions of amounts of amplified nucleic acid copies with a given label based on the determined amounts of step d), the probability of the labels of attaching to a nucleic acid, an estimated amplification efficiency or expected number of nucleic acid copies in the sample, and based on the expected duplication of amplified nucleic acid copies with a label in a nucleic acid duplication procedure per duplication cycle depending on said estimated amplification efficiency,
(ii) determining the likelihood of the determined amount of nucleic acid copies with the labels to occur according to the modelled probability distribution of nucleic acid copies with the labels,
(iii) maximizing a likelihood of step (ii) by varying the estimated amplification efficiency or expected number of nucleic acid copies in the sample,
(iv) providing the estimation of the number of nucleic acid copies in the sample according to said maximized model or according to the estimated amplification efficiency at the maximized model.

The invention further provides a computer program product comprising computer readable instructions for calculating an estimation of the amount of nucleic acid copies in a sample based on a determined amount after an amplification of nucleic acids with attached labels according to step e) of the inventive method.

All embodiments and aspects of the invention can be combined and all preferred and explained embodiments refer to all aspects of the invention alike. I.e. preferred embodiments of the methods also read on preferred embodiments of the computer program product and vice-versa.

DETAILED DESCRIPTION OF THE INVENTION

The present invention is described in the above summary section and in the claims. Several expressions are used, which for ease of reference and synopsis with the examples are explained in connection with the variable designations used in the examples.

"nucleic acid copy number" and "nucleic acids of a number of copies" ("K") refer to an amount, abundance or concentration of nucleic acid molecules of a shared same sequence, which are referred to as nucleic acid copies. As used herein, the term "copy number" is used to indicate the amount, abundance or concentration before amplification, i.e. in the original sample. This is the amount or copy number to be determined by the inventive method. Such a sample may have different nucleic acid molecules of different quality and/or sequence. These are referred to as nucleic acids of a different species. All nucleic acid molecules of the same species (without label) are refered to as "pool". Different "pools" of nucleic acid molecules are different nucleic acid molecules of different species, each species forming its own virtual pool. "Pool" does not require a physical separation, all nucleic acid pools or species may be in the same sample.

"Variable labels" refers to labels of different property or species that can be identified. An example are random nucleotide labels, such as random mono nucleotides (i.e. a mixture of A, T (U), G, C), random dimers (i.e. a mixture of AA, AT, AG etc. to CC), random tri-, tetra-, penta-, hexa-, septa, octa-mers, or longer nucleotides. Such label mixtures have various different labels, each specific label being possibly represented once or more than one time. In case of random nucleotides, the constitution of the label mixture may have none to multiple copies of a given label, depending on the size of the label mixture pool. Labels are attached to nucleic acid molecules. Said attachment may suffer from inefficiency, meaning that less than all nucleic acid molecules are labelled. Labels are referred to by the indicator "b".

"Probability of the labels of attaching to a nucleic acid copy" ("$p_b$") quantifies said inefficiency as a probability of attaching a label to a nucleic acid molecule. This quantification is usually an estimation in the methods according to the invention.

A "nucleic acid duplication procedure" is a procedure that creates a duplicate of a nucleic acid. Such a method may comprise the steps of annealing a primer and extending said primer in a template depending fashion, like PCR. Such methods may suffer from inefficiency, meaning that less than all starting nucleic acid molecules are duplicated (i.e. "amplification efficiency" is <1, with 1 being the theoretical ideal case of each nucleic acid molecule being duplicated and 0 meaning that no nucleic acid molecule is duplicated).

"Estimated amplification efficiency" ("$p_d$") is an estimate of said amplification efficiency, which is obtainable in the inventive calculation procedure. The estimate is a likely amplification efficiency that varies from nucleic acid species to species due to the inherent amplification bias causes (foremost different nucleic acid sequences). The inventive estimation model reflects said different amplification efficiencies between nucleic acid species.

"Amounts of amplified nucleic acid copies with a label" ("$n_b$") refers to the quantifiable amounts or concentration of nucleic acid copies that comprise a label after amplification. The label species is indicated by the subscript "b" in the variable and formula depiction. The expression refers to nucleic acid copies and therefore relates to one nucleic acid species that has produced identical copies. Of note, and to stress its importance, the nucleic acid molecules of one species (or "pool") may have different labels attached to them. In fact, attaching different labels is important in the inventive method in order to determine label attachment efficiencies and in turn monitor amplification efficiencies within the inventive method. These different labels may be attached indiscriminately to all kinds of nucleic acids in the sample. The plural in "amounts" indicates that different amplified nucleic acid copies with a label can be determined. As said, "nucleic acid copies" refers to the same nucleic acid species. The difference is due to the label which is different between individual molecules, although as said multiple labels of the same label species may also be attached to the nucleic acid molecules. This is expressed by "each amount is determined for nucleic acid copies with a different label". According to the estimation procedure of determining the amount of a given nucleic acid species (also copy number in the sample), "$n_b$" also refers to the amount of labels on said nucleic acid copies (nucleic acid molecules of said species or "pool"). Accordingly, the expression "amounts of said label" ("$n_b$") is also used with "b" indicating the label. The amount of amplified nucleic acid copies with a label in a pool under investigation together is referred to as "N". It is the sum of individual amounts of label "b" ($n_b$).

"Estimation of the nucleic acid copy number in the sample" ("K" or "$K_{est}$" with "est" for "estimated" emphasizing the estimated nature) relates to the estimation of the nucleic acid copy number in the sample by the inventive method. Estimate may differ from the actual natural amount in the sample, whereas said difference or error is strongly reduced in comparison with prior art methods. A further benefit of the inventive method is that label biases, e.g. introduced by low label variety and labelling inefficiencies, are greatly reduced. The expression "expected number of nucleic acid copies in the sample" indicates that the inventive method is a refinement of expectations with each iteration generating a new expected value, with the final "expected" value being referred to as the estimate. $K_i$ or $K_{i+1}$ denote the ith or i+1th iteration. Numbers of nucleic acid copies with a label before amplification, i.e. after label attachment are referred to by a lower case "k" in the formulas, or "$k_b$" with "b" indicating the label species. This term usually refers to nucleic acids with the same base nucleic acid sequences as in the sample (same "pool") but differ by the attached label. In other words, $K_{est}$ is the sum of all nucleic acid estimates per label [$k_b$] summed for all labels that are used in the calculation. [$k_b$] in turn is the result of labelling according to labelling probability [$p_b$] (see also examples, formulas (5) and (2)—$K_{est}$ and $p_b$ are connected via equation (3); there $K_{est}$ is an approximate solution to equation (3)).

"Number of distinct detected labels in step d)" ("DU") refers to the number of detected distinct labels of different quality, such as a different barcode or sequence. Accordingly, it refers to the number of distinction or number of species types, but not to the amount of the labels of each specific label species.

"Expected duplication of amplified nucleic acid copies with a label" refers to modelled duplication in an amplification reaction, which, due to inefficiency, is not duplicating each nucleic acid molecule per cycle of amplification. A probability function will result in accordance with statistical duplication per cycle. The number of amplification (or duplication) cycles is given as "c".

"Modelled probability distribution of nucleic acid copies with the labels" ("$p(n_b)$") refers to the above-mentioned modelling of the result of an amplification process in terms of nucleic acid copies with the labels ("$n_b$"). A probability of arriving at a certain amount after amplification is calculated. The collective probabilities for various amounts are combined in a probability distribution (over the amount values). Such a probability distribution function may have a Gaussian shape or other shape and may have a maximum resembling the maximum probability that the nucleic acid copies with the labels will have this amount at the maximum value. The shape of the distribution function may have a global maximum and one or more local maxima. The generation of said probability distribution is dependent on the estimated amplification efficiency or the expected number of nucleic acid copies in the sample (these two are interconvertible) and the model can be adjusted by varying and refining expectations of one of these two parameters, which is used in maximizing the likelihood or probability to best fit the distribution function with the observed amounts over all nucleic acid copies with a label under investigation (which do not need to be all nucleic acids in the sample or all labelling products).

"Determined amounts of amplified nucleic acid copies" ("N") refers to the total amount over all nucleic acid copies under investigation. Note the plural in "copies" that refers to the qualitative plural of distinct copies.

According to this synopsis, the inventive method can also be written together with the assigned variable indicator in brackets next to the assigned element in square brackets as: method of estimating a [nucleic acid copy number] (K) after amplification comprising the steps of a) providing a sample comprising nucleic acids of a to be determined [number of copies] (K);

b) attaching variable labels to said nucleic acids;

c) amplifying said nucleic acids with the labels with a nucleic acid duplication procedure;

d) determining [amounts of amplified nucleic acid copies with a label] ($n_b$), each amount is determined for [nucleic acid copies with a different [label] (b)] ($n_b$ for different bs); and e) providing an [estimation of the nucleic acid copy number in the sample] ($K_{est}$) of step a) based on the determined [amounts of step d)] ($n_b$) by approximating a [probability of the labels of attaching to a nucleic acid] ($p_b$) by for at least two, preferably at least four, at least ten or more, different nucleic acid species in the sample: averaging the [amounts of said label] ($n_b$) for different nucleic acid species after amplification; and iteratively or stepwise (A)

refining an [estimated or expected number of nucleic acid copies in the sample] ($K_{est}$) based on the [number of distinct detected labels in step d)] (DU) and the expectation of the number of different labels to attach to a nucleic acid according to the [probability of the labels of attaching to a nucleic acid copy] ($p_b$) and a previous iteration or pre-set value of an [expected number of nucleic acid copies in the sample] ($K_{est}$) or an [estimated amplification efficiency] ($p_d$); or (B)

(i) modelling [probability distributions of amounts of amplified nucleic acid copies with a given label] ($p(n_b)$) based on the determined [amounts of step d)] ($n_b$), the [probability of the labels of attaching to a nucleic acid] ($p_b$), an [estimated amplification efficiency] ($p_d$) or [expected number of nucleic acid copies in the sample] ($K_{est}$), and based on the expected duplication of amplified [nucleic acid copies with a label] ("pool") in a nucleic acid duplication procedure per duplication cycle depending on said [estimated amplification efficiency] ($p_d$), (ii) determining the likelihood of the [determined amount of nucleic acid copies with the labels] ($n_b$) to occur according to the [modelled probability distribution of nucleic acid copies with the labels] ($p(n_b)$), (iii) maximizing a likelihood of step (ii) by varying the [estimated amplification efficiency] ($p_d$) or [expected number of nucleic acid copies in the sample] ($K_{est}$), (iv) providing the [estimation of the number of nucleic acid copies in the sample according to said maximized model] ($K_{est}$) or according to the [estimated amplification efficiency] ($p_d$) at the maximized model.

The inventive method is based on a sample comprising nucleic acids of a to be determined number of copies. The sample may comprise various distinct nucleic acid species, each species being represented by one or more molecules or "copies". For example, the sample may comprise 1, 2, 3, 4, 5, 6, 7, 8, 9, 10, 20, 30, 50, 100, 150, 200 or more or any range between these values of distinct nucleic acid species. The copy number of at least one or more species may be 1, 2, 3, 4, 5, 6, 7, 8, 9, 10, 20, 30, 50, 100, 150, 200, 1000, 10000, 20000 or more molecules or any range between these values of a copy number.

The nucleic acids may be full-length natural nucleic acid molecules, like mRNA, microRNA, rRNA, tRNA, or genomic or vector nucleic acids, like genomes (preferably short ones, like viral or bacterial genomes or their molecular parts), vectors like plasmids or transposons or artificial DNA constructs. In general, the nucleic acid may be RNA or DNA or any other nucleic acid type that can be amplified.

Preferably, the nucleic acids are fragments of a larger nucleic acid of origin, such as fragments that are produced in next generation sequencing (NGS) or RNA-Seq or shotgun sequencing. Fragmenting may be by physical means, like shearing, or by chemical or enzymatic means, like restriction enzyme cutting. Fragmentation may be random, i.e. no site-specificity for cutting which will yield random fragments, or it is site-specific, such as specific for selected nucleic acid pattern, like enzymatic restriction. Random fragmentation will yield many different nucleic acid species, which can be handled by current sequencing methods assisted by computational procedures.

Preferably, the nucleic acids of the sample to be analysed by the inventive method (e.g. fragments or other nucleic molecules as above) have an average length of 10 to 10000 nucleotides (nt), preferably of 15 to 8000 or of 20 to 5000 or of 50 to 4000 or of 80 to 3000.

In step b) variable labels are attached to said nucleic acids. Attachment can be facilitated by known chemistry or enzymatic reactions, such a ligation reaction or binding reaction. Attachment facilitates that the label remains adhered to the nucleic acid throughout the procedure until detection in step d). Any label that is suitable to label nucleic acids can be selected. It is necessary that the label is also attached to duplication products in the amplification reaction in step c). The most convenient label are therefore nucleic acid tags, like barcodes or UMIs. However, with additional effort also other labels like proteins or peptides, peptidic nucleotides, antibodies, receptors, antigens, recognition molecules (which can be identified by a binding partner, like biotin and avidin, fluorescent labels), quantum dots etc. can also be used. Preferred are labels that allow high variability. Also for this reason, nucleotidic labels are preferred, but they are not the only possibility.

Preferably, the label is capable of amplification, especially a macromolecule capable of being amplified as disclosed in WO2017/051387 A1.

In case of nucleotide labels, these can be RNA or DNA or any other nucleotide type. It may be the same type as the nucleic acid molecules or another type. Nucleic acid labels use unique properties of the label molecule as recognition element. Preferably, said recognition element is the nucleotide sequence. Nucleotides may be selected from A, T(U), G, C, or any combination thereof, preferably all four nucleotide types (U is preferable used on RNA, T preferably used on DNA; both are recognized by complementary A). The label may comprise 1, 2, 3, or 4 different nucleotide types. With only one nucleotide type, the recognition element is essentially the size or length of the label. Including more nucleotide types allows many permutations, such as $4^6$ (4 exp 6) for a label of 4 different nucleotide types of 6 nucleotides in length. The number of permutations follows the formula nucleotide type number to the exponent of the (nt length), such as $4^3$, $4^4$, $4^5$, $4^6$, $4^7$, $4^8$ etc. or $3^3$, $3^4$, $3^5$, $3^6$, $3^7$, $3^8$ etc for 3 types of nucleotides. A suitable number of distinct labels can be selected by the practitioner according to the complexity and diversity of nucleic acids expected in the sample of interest. For example, 2, 3, 4, 5, 6, 7, 8, 9, 10, 15, 20, 25, 30, 35, 40, 50, 60, 70, 80, 100, 120, 140, 160, 180, 200, 300, 400, 500, 750, 1000, 2000, 5000, 10000 or more or any range between these values of distinct label numbers are used. In some methods, especially method (A), preferably the number of distinct labels is selected so that it is greater than the number of an expected nucleic acid copy number. This is also possible in method (B) but not necessarily. Method (B) is better capable to deal with lower numbers of distinct labels.

The labels are not required to be provided as molecules, but it is also possible to have various copy numbers of the labels. The inventive method has the power to cancel out any labelling bias, i.e. inhomogeneous concentrations of the various labels and any bias due to inhomogeneous attachment of the labels to the nucleic acid molecules. Preferably, the individual label species have copy numbers of 1, 2, 3, 4, 5, 6, 7, 8, 9, 10, 50, 100, 1000, 10000 or more e.g. preferably up to 1 Million (M), up to 100000 or up to 10000. Preferably, the total number of all labels shall equal or exceed the number of all nucleic acids of all species so that each nucleic acid under investigation is labelled. The total copy number of all labels together may be at least 1000 or 10000 or more e.g. preferably up to up to 10000 Million (M), up to 5000 M, up to 1000 M or up to 500 M.

In preferred embodiments, labels are used that allow the detection and correction of errors in the label sequence. Such error correction labels are per se known in the art as described in Krishnan et al., Electronics Letters, 2011, 47, 236-237. These labels are useful to detect sequencing error during sequencing of the label sequence—within the error margin of a given sequencer. For example, when we consider two labels with sequences ACGT and TGCA, then we can correct one error in these labels where one nucleotide is replaced with another one because the labels differ in all 4 positions. If, for instance, the first label read-out is changed to ACCT and the second to TCCA (both due to sequencing errors), then the incorrect labels have a distance of one from their correct version but a distance of three from the correct version of the other label. Hence, based on their distance from the correct labels, ACCT would be correctly assigned to ACGT, and TCCA to TGCA. If, on the other hand, the first and second label would both be changed to ACCA, then this would have a distance of two to both correct labels. Hence, we could not correct the error but only infer that more than one error has occurred. Consequently, the labels ACGT and TGCA are one-error-correcting and two-error-detecting. This example refers to the correction of substitution errors (see Krishnan et al., supra; and Bystrykh et al., PLOS ONE, Public Library of Science, 2012, 7, 1-8; all references included herein by reference). Longer labels with greater nucleotide difference between all different labels allow correction and detection of more errors. It is also possible to generate labels correcting substitutions, insertions and deletions (Buschmann et al., BMC Bioinformatics, 2013, 14, 272; Hawkins et al. Proceedings of the National Academy of Sciences, National Academy of Sciences, 2018, 115(27): E6217-E6226; all references included herein by reference). Preferably such error correcting labels are used in step b) of the inventive method. Especially preferred, the error correcting labels are substitution-, insertion- and deletion-correcting labels. In particular preferred, in combination therewith or as alternatives, the error-correcting labels are suitable for correcting 1, 2, 3 or more errors. Such labels could have a sequence difference by 2n+1, with n being the number of errors that should be correctable. Preferably the sequence difference is 2n+2. Said additional difference in comparison to formula 2n+1 would add another layer of error-detection on top of error correction amounts as in the above example.

Preferably, in step d) error correcting is used to assign the correct label (without sequencing error). Pure error detection (without correction) would be used to remove such labels from further analysis.

Step c) comprises amplifying the labelled nucleic by a nucleic acid duplication procedure, such as PCR. Nucleic acid amplification procedures usually follow the pattern that for a given template labelled nucleic acid, a (further) copy is produced. Such a method may comprise primer binding and extending said primer. The step of primer binding may require the attachment of a linker or adapter molecule with a primer binding region. This has the advantage that any nucleic acid sequence can be amplified starting from the beginning or end. Other but less preferred sequence-independent priming is random priming. As stated in the background section, nucleic acid amplification methods tend to suffer from inefficiency, and even a sequence bias of said inefficiency. This bias is usually not known. The invention essentially provides a workaround to compensate such an unknown bias and inefficiency.

The mode of amplification, i.e. duplication in usual cases, is modelled and considered in the inventive calculation steps. If the mode of amplification would be different, such as triplication or other x-fold amplification per amplification cycle, then this could be considered as well in the inventive method. Since the standard method of amplification, like PCR, is duplication per cycle, the invention has been written with regard to duplication. Of course, the invention also reads on other x-fold amplification per cycle instead. Of course, more than one cycle of amplification are usually used. Accordingly, a duplication method may yield a many-fold amplification in total. Preferably, 2, 3, 4, 5, 6, 7, 8 9, 10, 11, 12, 13, 14, 15, 16, 17, 18, 19, 20, 21, 22, 23, 24, 25, 26, 27, 28, 29, 30 or more amplification cycles are used.

Step d) comprises determining amounts of amplified nucleic acid copies with a label, each amount is determined for nucleic acid copies with a different label. The determination of amounts usually comprises identification or separation of the nucleic acid copies with a label to deduce the nucleic acid's amount in a mixture. The label, which may and usually is different from molecule to molecule is likewise identified together with the identity of the nucleic acid species. An example method includes sequence determination, which together with the sequence of the nucleic acid molecule, also provides its identity, which then can be counted. Accordingly, the step provides the amount of nucleic acid copies (together with the labels) after amplification. Now it is the goal to arrive at the amount or number before amplification, which is done in step e).

According to step e), the inventive method provides two alternative detailed methods, termed (A) and (B), which are further supported by examples 2.1.2 and 2.2, respectively. In general, also for both methods (A) and (B), an estimation of the nucleic acid copy number in the sample of step a) is provided based on the determined amounts of step d) by approximating a probability of the labels of attaching to a nucleic acid by for at least two, preferably at least four, at least ten or more, different nucleic acid species in the sample: averaging the amounts of said label for different nucleic acid species after amplification. The step of averaging amounts of said label again refers to a copy number of concentration of the label that is averaged over different nucleic acid species (or fragments) for the various labels that are used in the inventive method. Accordingly, it can be determined how often a specific label has been attached to a nucleic acid molecule—independent of the nucleic acid species because it is averaged. Given that label attachment to different nucleic acid species may differ, since this is a stochastic effect and follows statistical variability further influenced by attachment inhomogeneity of labels and attachment reactions. In order to get an average, averaging is done for at least 2 nucleic acid species, preferably more than 2, such as 3, 4, 5, 6, 7, 8, 9, 10, 20, 30, 40, 50 or more different nucleic acid species or any range in between these values. This average can then be used in determining label attachment probability (also referred to as "probability of the labels of attaching to a nucleic acid copy") or an expectation of the number of different labels to attach to a nucleic acid. Such a probability or expectation can be calculated according to standard statistical methods taking said average and the deviation from said average for the individual label attachment for the specific nucleic acid species (i.e. the members that are averaged) into account. This means that the number of labels also depends on the label attachment reaction kinetics and any inhomogeneities in the label mixture composition, possibly with some labels being overrepresented as compared to others. Once the amplification efficiency is known (for a given nucleic acid species), it is possible to directly calculate the original number of nucleic acids in the sample with the determined amount after amplification (see formula (27) in the example section). In cases where amplification efficiency is not directly derivable, it is possible to iteratively approximate said amplification efficiency. Since amplification efficiency is directly related to the number of nucleic acids, said number can equivalently be fed into the calculation instead of or in addition to amplification efficiency. In fact, according to preferred embodiments, the estimated amplification efficiency or expected number of nucleic acid copies in the sample are used interchangeably. They can be converted according to formula (27). Thus, whenever the inventive method uses the expression "estimated amplification efficiency" said expression also refers to "expected number of nucleic acid copies in the sample" and vice-versa.

Preferably, the efficiency of amplifying said nucleic acids with the labels in said nucleic acid duplication procedure is not 100%. It may be different for different species of nucleic acid copies—a difficulty, which the inventive method takes account of and compensates inherently. Usual amplification efficiencies are from 60% to 99.99%, preferably, 65% to 99%, e.g. 70% to 95%, most commonly around 80%. Example average variations between different species of nucleic acid copies are up to +/−20% or up to +/−10%.

The present invention provides the estimation of the nucleic acid copy number in the sample in an iterative process. This means that temporary estimates or expectations of the nucleic acid copy number are improved step-wise, usually in repeated fashion until a final estimation of the nucleic acid copy number is reached. In an alternative to a step-wise improvement, a "brute-force" approach is also possible, wherein various nucleic acid estimates are calculated (in intervals or stepwise covering the entire possible or reasonable range, e.g. from 1 to the total amount of all combined nucleic acid species amounts determined in step d) ("N")), and the best model of all these estimates is selected. The iterative process can be stopped by the practitioner, when he/she is satisfied with the improvement, which is usually after convergence or if a sufficient number of expectations has been estimated by selecting the best fit. Convergence is for example—also set by the practitioner when he/she is satisfied—, e.g. when an iteration does not change the estimation of the nucleic acid copy number or changes it by 5% or less, such as 3% or less or 1% or less or 0.5% or less or 0.3% or less. Other parameters used in the inventive method may be used as well in the decision to stop the iteration, such as a determined amount of nucleic acid copies with the labels (after amplification) to fit with a particular amplification model. Said model can then be used to calculate the nucleic acid copy number in the sample. The invention comprises an iterative refinement towards a maximum estimated number of nucleic acid copies in the sample. Many maximisation procedures are known in the art and can be used according to the invention. A possible example iteration procedure splits the amplification efficiency interval of 0 to 1 into evenly spaced subintervals. From these subintervals one or more is selected such that the likelihood at the boundaries of the selected subintervals is higher than at the boundaries of the not selected subintervals. On each of the selected subintervals a binary search [4] is performed which finds the amplification efficiency with the highest likelihood in the interval. The overall maximum is the maximum of the results of the binary searches. The number of subintervals can be 1 to N, and the binary search can be performed in 1 to N subintervals. Of course, many other methods for maximization are also possible. Again, the expected number of nucleic acid copies in the sample can be used instead of an estimated amplification efficiency, which can be used interchangeably. In the examples, $K_{est}$ is the value which (approximately) fulfills equation (3), where the right-hand side of (3) is defined via (2). There are many methods, known to people skilled in the art, for solving a non-linear equation such as (3), e.g. non-linear optimization or non-linear programming. An example is a fixed-point iteration according to equations (4) and (5).

A particular embodiment of the invention, termed method (A), comprises refining an estimated or expected number of nucleic acid copies in the sample (i.e. the intermediate until a final estimated value is determined after iteration). Said refining is based on and using the number of distinct detected labels in step d) and the expectation of the number of different labels to attach to a nucleic acid according to the probability of the labels of attaching to a nucleic acid copy and a previous iteration or pre-set value of an expected number of nucleic acid copies in the sample or an estimated amplification efficiency (as said above, these two "or" variants can be used interchangeably). The number of distinct detected labels in step d) is a measured value and needs no further explanation (otherwise we refer to the terminology section and step d) above). The expectation of the number of different labels to attach to a nucleic acid according to the probability of the labels of attaching to a nucleic acid copy or written with the variable terminology for better reference: the expectation of the number of different labels to attach to a nucleic acid according to the [probability of the labels of attaching to a nucleic acid copy] ($p_b$) or "label attachment probability", essentially refers to an expectation of labelling efficiency, that can be calculated as mentioned above based on an average of the amounts of said label for different nucleic acid species after amplification. The probability of the labels of attaching to a nucleic acid copy can be used to calculate an expectation of the number of different labels to attach to a nucleic acid due to its correlation, i.e. the probability directly correlates with the expectation. A mathematician with skill in statistics and probability operations is able to perform such a calculation. An example is given by formula (2) herein in the example section. We also refer to the above section on the introduction to step e). The final parameter is either the pre-set value of an expected number of nucleic acid copies in the sample or an estimated amplification efficiency, or both in a combined model. The first iteration usually starts with a pre-set value. Further iterations can start with the value of the previous iteration. Usually, a practitioner providing the sample has a good guess of a supposed value and can use this in the inventive method. Other good starting values are based on common or usual amplification efficiencies. For example, it is possible to select a pre-set value for a first iteration of an expected number of nucleic acid copies in the sample or an estimated amplification efficiency in the range of the value of the number of different detected labels in step d) or by an integer ranging from 1 to the determined amounts of amplified nucleic acid copies. This embodiment is also written as follows with the parameter expressions in brackets and variable numbers as used in the examples for better reference: a pre-set value for a first iteration of an [expected number of nucleic acid copies in the sample] ($K_{est}$) or an [estimated amplification efficiency] ($p_d$) is selected from the value of the [number of different detected labels in step d)] (DU) or by an integer ranging from 1 to the [determined amounts of amplified nucleic acid copies] (N). Since the method provides iterative improvement, the starting or pre-set value is not too important. The $K_{est}$ value will improve continually. Far deviating starting pre-set values will just need further iterations to arrive at the same final quality as a comparative process starting with a better starting or pre-set value. The method of alternative (A) is further illustrated in example 2.1.2 and the formulas shown therein, which can be used according to the general invention described herein.

The inventors have also provided an even further improved method to calculate the number of nucleic acid copies in the sample. This method is also iterative and uses said average of the amounts of said label for different nucleic acid species or the probability of the labels of attaching to a nucleic acid.

Method (B) essentially comprises four steps, termed (i) to (iv). The method usually comprises (i) modelling probability distributions of amounts of amplified nucleic acid copies with a given label. It is also possible to use the sum of the amounts of individual nucleic acid species together, i.e. the amount of amplified nucleic acid copies with a label for all nucleic acid species ("pools") under investigation, instead or in addition. We refer to the terminology section above. Briefly, a model of the amplification process is created, which takes the mechanics of amplification into account that is in turn dependent on the theoretical amplification rate per cycle (usually duplication), cycle number and amplification efficiency and models these behaviours given that amplification efficiency of the wet-chemical reaction is unknown. Instead the method uses the determined amounts of the nucleic acids (with labels) of step d) (a known determined value), the probability of the labels of attaching to a nucleic acid (an approximated value as determined above; this is a step common with method (A)), an estimated amplification efficiency or expected number of nucleic acid copies in the sample (which are used interchangeable as above, these values are again iteratively improved), and based on the expected duplication of amplified nucleic acid copies with a label in a nucleic acid duplication procedure per duplication cycle depending on said estimated amplification efficiency (i.e. the model of the amplification process). Such models are generally known in the art. Amplification methods have been widely studied and the statistical amplification rate after a known number of cycles in an (inefficient) duplication or other x-fold enrichment process. We refer to the references [1], [2] and [3] and the example section at 2.2. Preferably, the expected duplication of amplified nucleic acid copies with a label is modelled in a Gaussian, negative binomial, Gamma, Dirac delta or Galton-Watson duplication probability function or a mixture thereof. Preferably a stochastic branching model is used in modelling probability distributions of amounts of amplified nucleic acid copies with a given label. Such a model takes the nature of a duplication amplification process into account, such as the Galton-Watson model. Models with low computational time requirements, are for example negative binominal or unimodal or multimodal distributions. Also, mixtures can be used to reduce computer calculation time, such as using such models with low computational time requirements for complex tasks, such as for providing a probability function for higher numbers of nucleic acid copies with a label ("k") values. Although said "k"-value as present in the sample may be unknown, a "k" value can be approximated as a variable according to equation (25) or (7) as the sum of the $p(n_b|k)$ weighted by $p(k|K, p_b)$. The latter is given by formula (26) or (8). Summing over a variable in a probability distribution removes this variable from the probability distribution. This is, usually, done with unknown variables. According to formula (25) $p(n_b|K)$ is a mixture of the $p(n_b|k)$ with weights $p(k|K, p_b)$. Equations (25) and (26) are special cases of equations (8) and (7). For example, higher numbers for k are a k of 5 or more, preferably 10, or more, e.g. 20, 30, 40, 50, 60 or more or any range between these values. Such a probability function is calculated for the various nucleic acid species of interest. Therefore, multiple probability distributions are obtained.

Step (ii) of method (B) comprises determining the likelihood of the determined amount of nucleic acid copies with the labels (as in step d)) to occur according to the modelled probability distribution of nucleic acid copies with the labels of step (i). In essence, this is a comparison of the model with the measured reality of step d). The likelihood of a statistical model given a data set is a well-known mathematical concept, see e.g. Pawitan, "In All Likelihood: Statistical Modelling and Inference Using Likelihood", (2003), Oxford University Press. In the examples, Different formulas are shown in examples 2.2.1 to 2.2.3 for different duplication models, in particular in example 2.2. the likelihood is given by formulas (9) and (10). In general, for each nucleic acid molecule species of interest, the measured value is compared with the probability distribution functions. The determined value of step d) will have a given probability, which may (or likely may not) be at a maximum likelihood or probability of said probability distribution functions. This offset may (and usually is) different for the individual nucleic acid species. Which leads to the next step:

Step (iii) comprises maximizing a likelihood of step (ii) by varying the estimated amplification efficiency or expected number of nucleic acid copies in the sample. Again, it is stressed that the "estimated amplification efficiency" and "expected number of nucleic acid copies" can be used interchangeably. Accordingly, only one parameter needs variation. The value is varied, e.g. randomly or deterministically, e.g. by moving the value into an expected direction by e.g. using further information such as iterative stepping or using the information of the probability distribution function—e.g. by moving uphill so that the determined value moves towards a maximum of a probability distribution function, etc.. Many methods for a maximisation process are known in the art and can be used for the invention.

Finally, in step (iv) the estimation of the number of nucleic acid copies in the sample is provided according to said maximized model of step (iii). The maximisation is e.g. reached at an iteration when the practitioner is satisfied with the improvement of the number of nucleic acid copies in the sample or when a convergence is reached as mentioned above at the introduction of step e). This concludes step e).

The invention further may comprise presenting the result of step e) on a readable medium, such as a printer output, a screen or written on a data carrier such as a computer memory device like a hard drive, flash memory or the like.

Generally, the invention is further illustrated in the examples and the formulas shown therein. These formulas can be individually used to illustrate the invention and further specify the inventive methods. For example, the probability of the labels of attaching to a nucleic acid ("$p_b$") can be determined according to formula (12), formula (45) or formula (46). The estimated amplification efficiency ("$p_d$") or the expected number of nucleic acid copies in the sample ("K" or "$K_{est}$") can be used interchangeable and can be converted according to formula (27). In method A), the probability distributions of amounts of amplified nucleic acid copies with a given label ("$p(n_b)$") can be determined according to formula (3), preferably by both formulas (4) and (5). In alternative B), the probability distributions of amounts of amplified nucleic acid copies with a given label ("$p(n_b)$") can be determined according to formula (25). All these formula uses are preferred embodiments of the invention—as are the examples, and can be combined with each other.

The invention further provides a computer program product employing the inventive method, e.g. containing machine code to perform or assist in said methods and steps on a computer. The computer program product can be provided on any kind of memory device. Also provided is a system, e.g. a computer device, programmed to assist in performing the steps of the inventive method. Calculation steps are usually performed without assistance of an operator. Input and setting steps may be assisted by the program or system, e.g. by suggesting an option proposal for the number random step repetitions, if desired. Of course, the program or system may also be performed with default parameters without further input from an operator. In particular, the invention provides a computer program product comprising computer readable instructions for or adapted for calculating an estimation of the amount of nucleic acid copies in a sample based on a determined amount after an amplification of nucleic acids with attached labels according to step e). In other words, the invention provides a computer-readable medium comprising instructions which, when executed by a computer, cause the computer to carry out at least steps e) of the inventive method. The data of the other method steps may of course be used in step e) as detailed above.

A computer readable memory device comprising a computer program product is adapted for performing a method according to the invention on a computer or for supporting a method according to the invention by a computer. Especially step e) may be performed on a computer. Even the usually wet-chemistry step a), b), c) and/ or d) may be assisted by a computer, e.g. to control and obtain data from an automated or semi-automated sequence reader. The computer program product or memory device may also be provided with a sequence generation component that obtains short sequencing reads from a sample, such as a sequencer, preferably a sequencer comprising a computer component. For example, computer readable media can include but are not limited to magnetic storage devices (e.g., hard disk, floppy disk, magnetic strips, . . . ), optical disks (e.g., compact disk (CD), digital versatile disk (DVD), . . . ), smart cards, and flash memory devices (e.g., card, stick, key drive, . . . ). Although possible, adaptation for performing steps a) to d) are or are not part of the computer program product. It is sufficient that the computer program product is able to receive input of determined amounts of amplified nucleic acid copies with a label, each amount being determined for nucleic acid copies with a different label—according to step d). Accordingly, the computer program product is adapted to perfrom step e) from said input. Also the nature (e.g. duplication method, like PCR) and preferably cycle number of the amplification and the potentially attached labels are used as input of the computer program product.

Accordingly, the invention also relates to performing step e) on a computer, in particular after the computer has received said input.

The computer program product may be adapted to presenting (including writing) or displaying the result of step e) on a readable medium, such as a printer output, a screen or written on a data carrier such as a computer memory device like a hard drive, flash memory or the like, e.g. as mentioned above. Likewise, the method of performing step e) on a computer preferably further comprises the step of presenting such a result of step e) on such a readable medium.

The present invention is further illustrated by the following figures and examples, without being limited to these embodiments of the invention. In particular embodiments, the invention provides methods which yield estimates with good accuracy of pre-PCR (or other amplification) nucleic acid numbers for unevenly distributed sets of labels (like barcodes, UMIs) or sets of labels which are too small for simple label counting. For this purpose we initially estimate the pre-amplification label distribution (FIG. 4) which is subsequently used in the estimation of the number of pre-PCR nucleic acids. First, we study a modification of label counting which uses the number of distinct observed labels after amplification as input but also takes the pre-amlification label distribution into consideration. The remaining methods rely on the post-amlipfication label frequencies as input and use statistical models to describe theamplification process (FIG. 5). We evaluate our methods on synthetic data generated for Poisson, Binomial and Galton-Watson models of the PCR process, as examples.

FIGURES

FIG. 1: Sequence specific PCR bias. Two pools of identical cDNA fragments (labeled cDNA1 and cDNA2) with the same size are amplified by PCR. After PCR their sizes differ. This can lead to inaccurate gene and isoform quantification.

FIG. 2: UMIs help identify fragment copies generated by PCR. UMIs are ligated to cDNA fragments before PCR. If the set of UMIs is sufficiently large, the same UMI will not be ligated to two copies of a cDNA fragment. In this case, the number of distinct UMIs after PCR is the same as the number of fragment copies before PCR.

FIG. 3: Correct estimation of pre-PCR pool sizes requires large sets of evenly distributed UMIs. If either the UMI set is too small or the distribution not uniform then the same UMI can be ligated to two different fragment copies. Counting distinct UMIs after PCR will lead to an underestimate of the number of pre-PCR copies.

Figure 4:
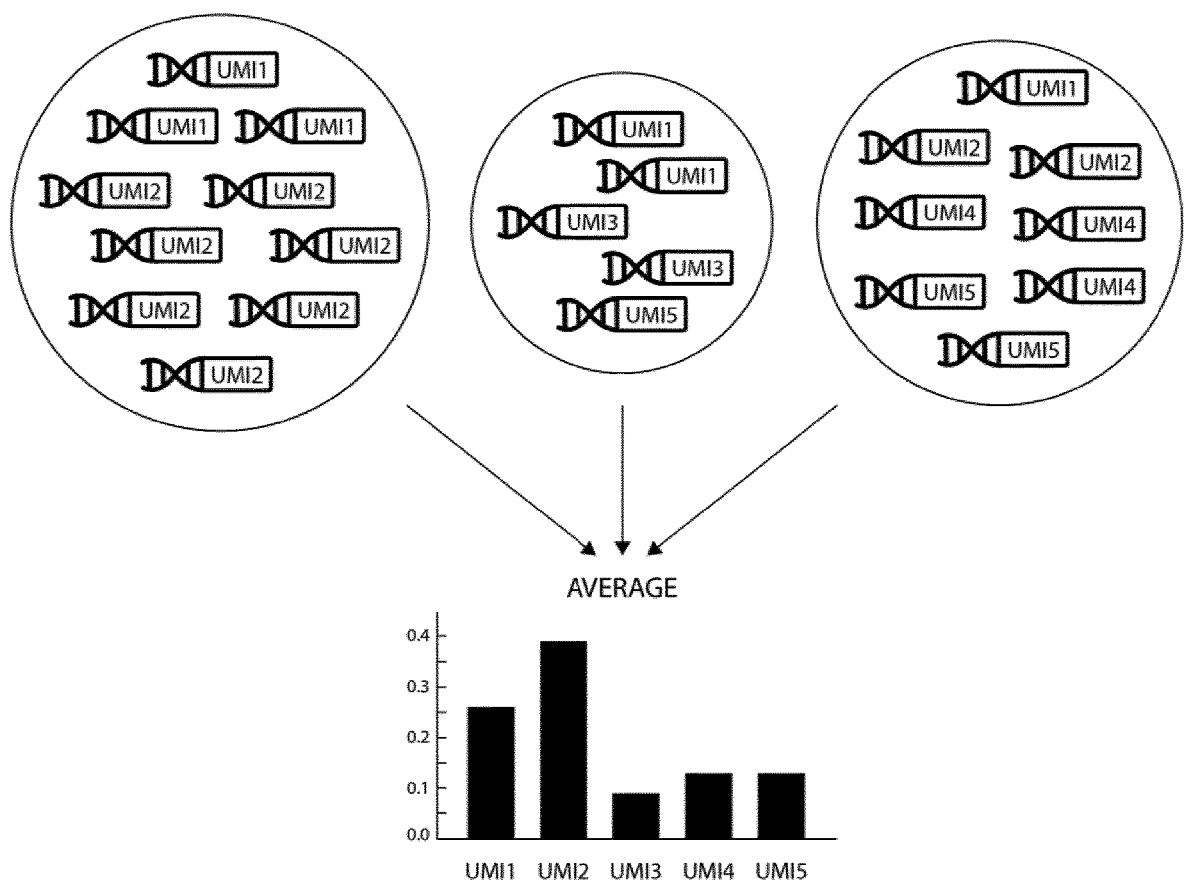
Figure 5:
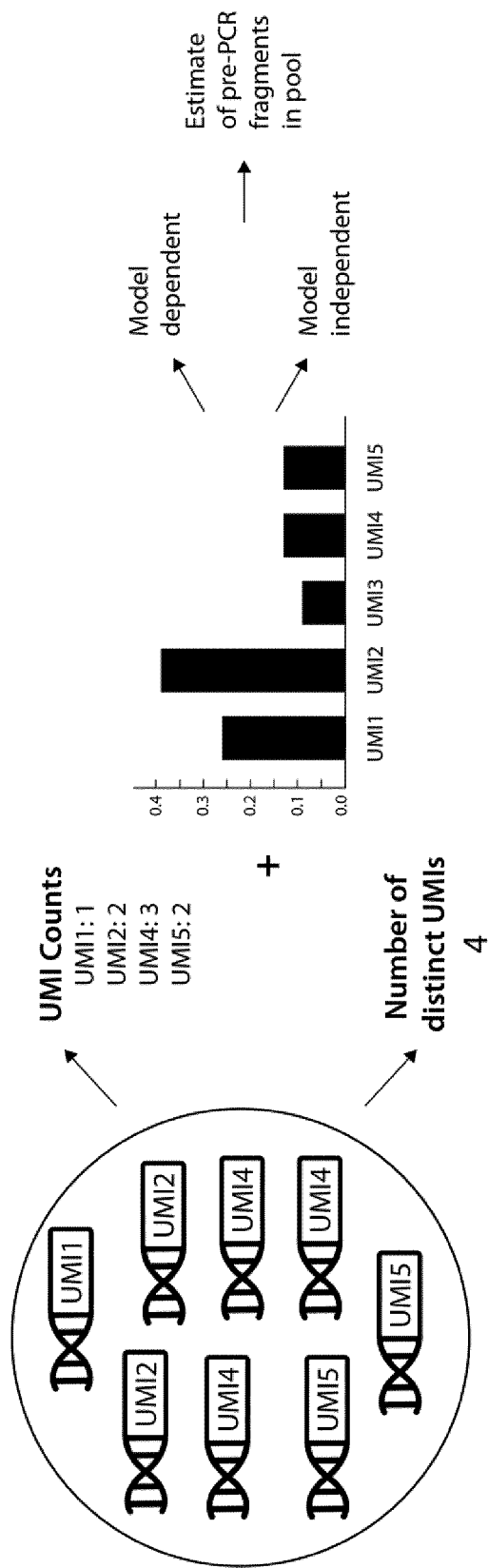

FIG. 4: The pre-PCR distribution of UMIs is estimated from the post-PCR UMI distribution in each pool. For this purpose the post-PCR frequency of UMI counts is averaged over all fragment pools.

FIG. 5: Estimating the pre-PCR number of fragments in a pool. Model dependent methods use UMI counts after PCR as input. Model independent methods use the number of distinct UMIs after PCR as input. Both types of methods use the estimated pre-PCR UMI distribution as input.

Figure 6:
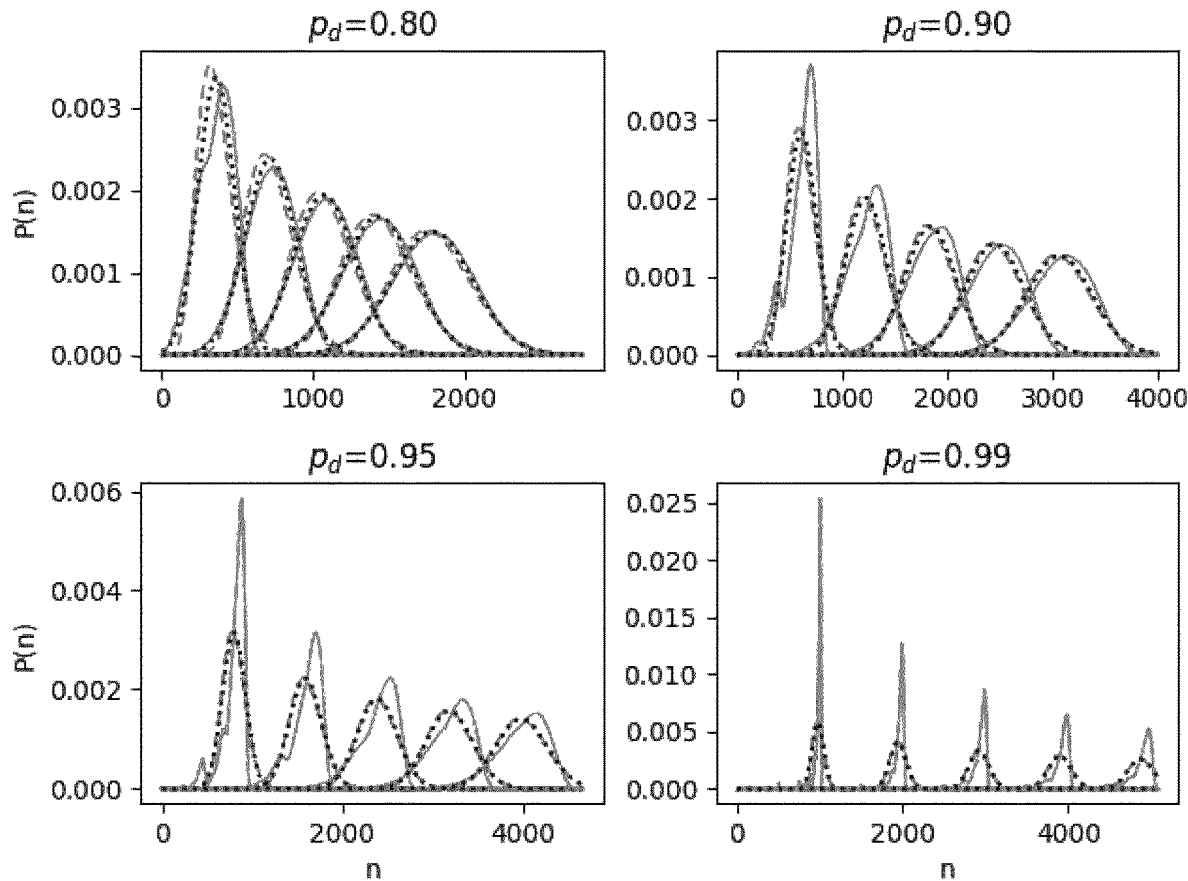

FIG. 6: Probability distributions $p(n|k, p_d, d)$ (solid lines) vs. approximations by negative binomial (dashed) and normal distributions (dotted). Each panel shows distributions for $k=1, \ldots, 5$. Peaks from left to right correspond to k in ascending order.

Figure 7:
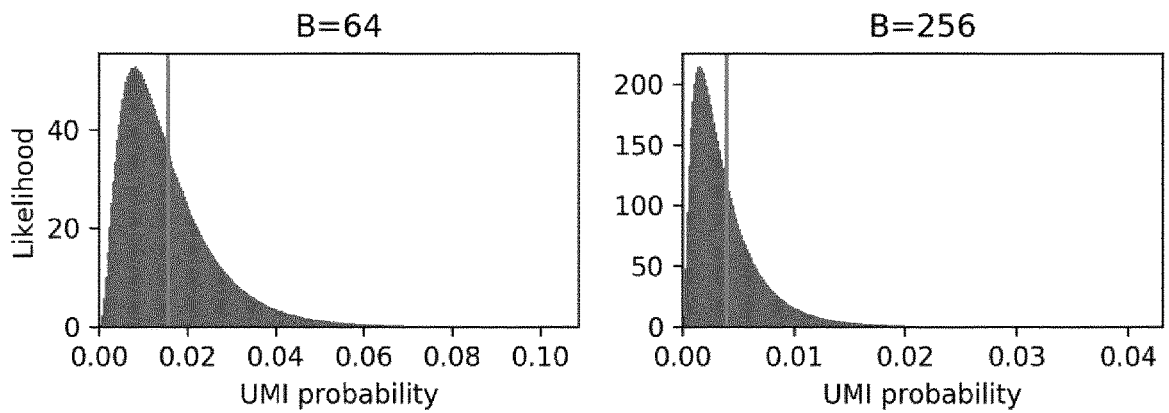

FIG. 7: Probability density function of UMI probability $p_b$. At each UMI position $(p_A, p_C, p_G, p_T)$ is sampled from to a Dirichlet distribution with $\alpha=5$. The UMI probability $p_b$ is given as the product of the probability of its nucleotides. The vertical orange line is located at $1/B$ on the x-axis, the value of $p_b$ for a uniform UMI distribution $\vec{p}$.

Figure 8:
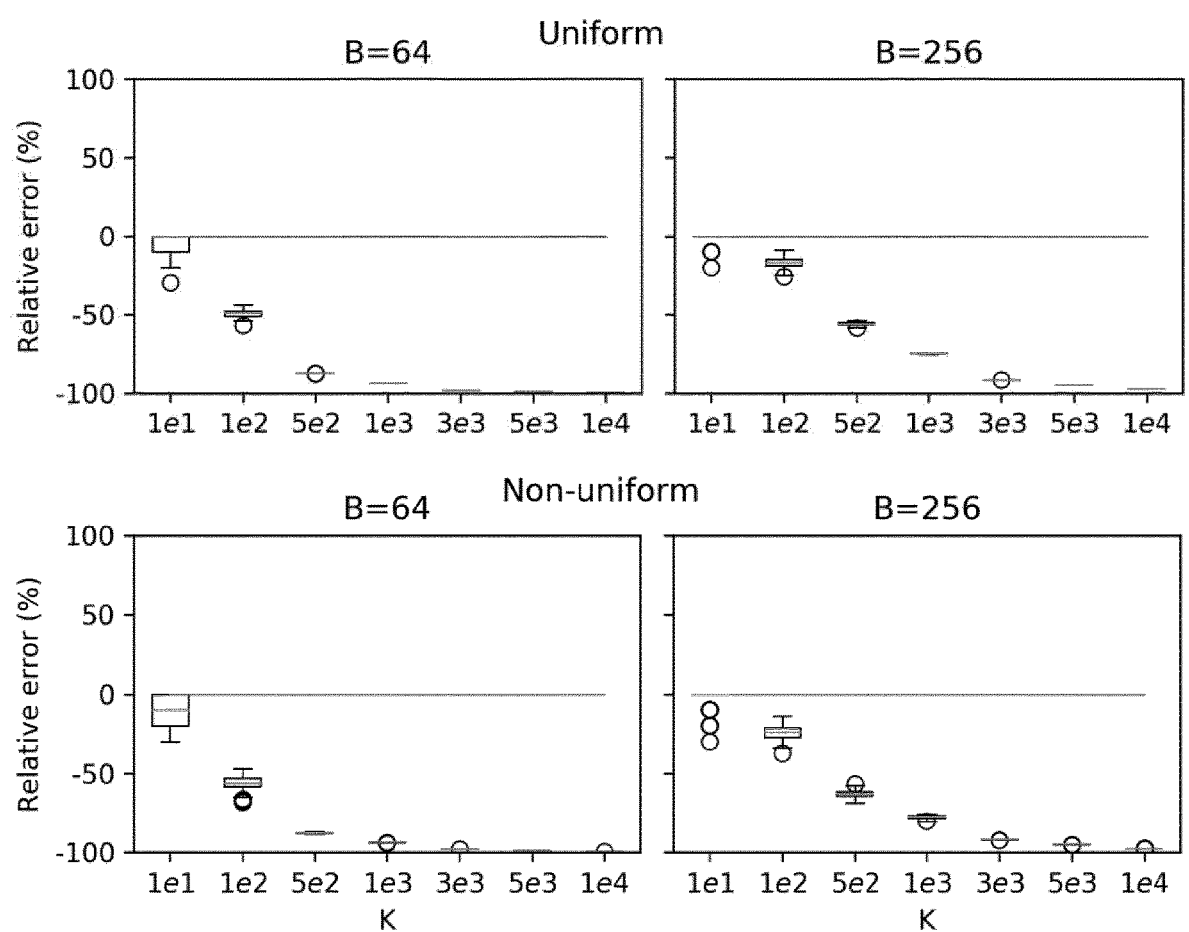

FIG. 8: Accuracy of UMI counting. Data from Binomial model. Type of UMI distribution (uniform/non-uniform) and number of UMIs B are given in the title of the graphics. Relative error of estimated number of pre-duplication fragments K on y-axis, true number on x-axis.

Figure 9:
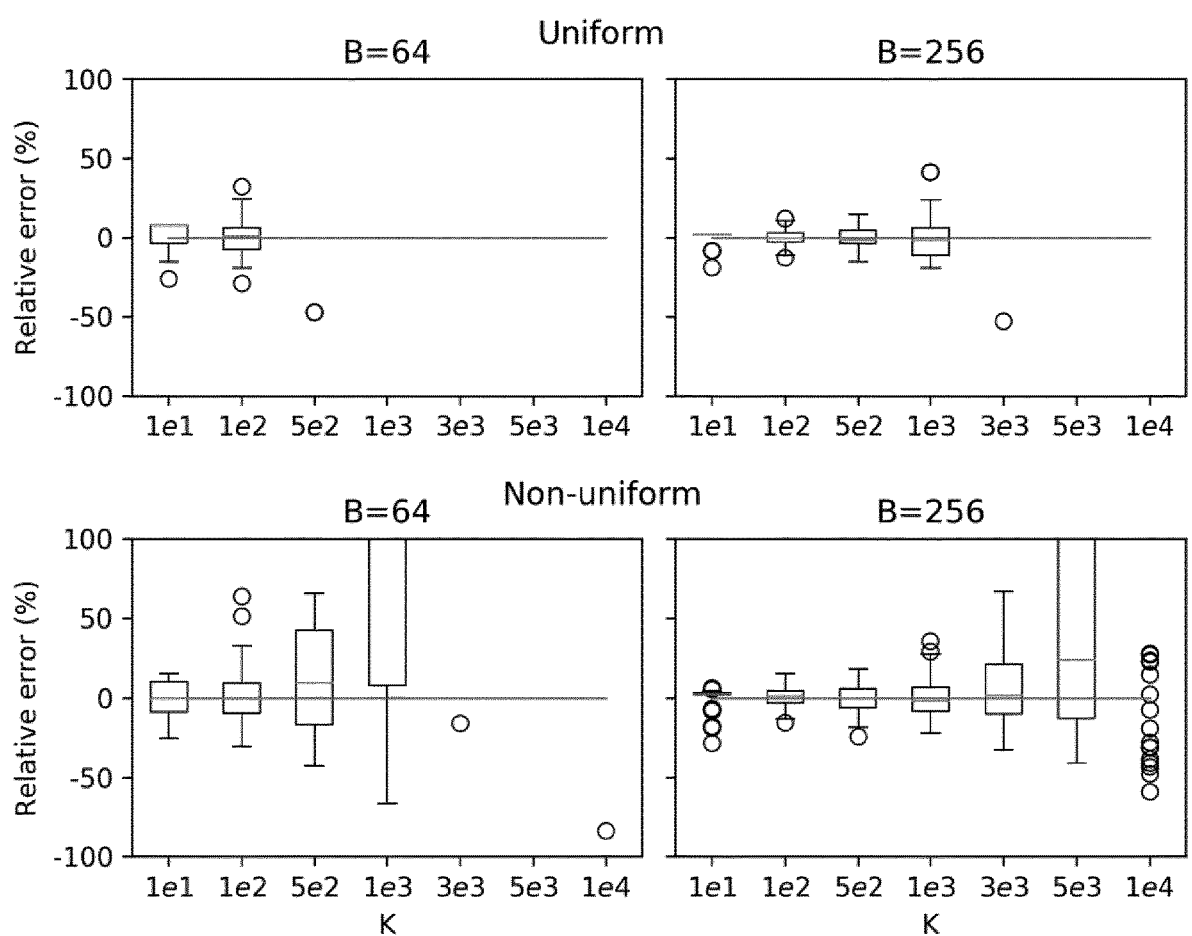

FIG. 9: Accuracy of frequency corrected UMI counting. Data from Binomial model. Type of UMI distribution (uniform/non-uniform) and number of UMIs B are given in the title of the graphics. Relative error of estimated number of pre-duplication fragments K on y-axis, true number on x-axis.

Figure 10:
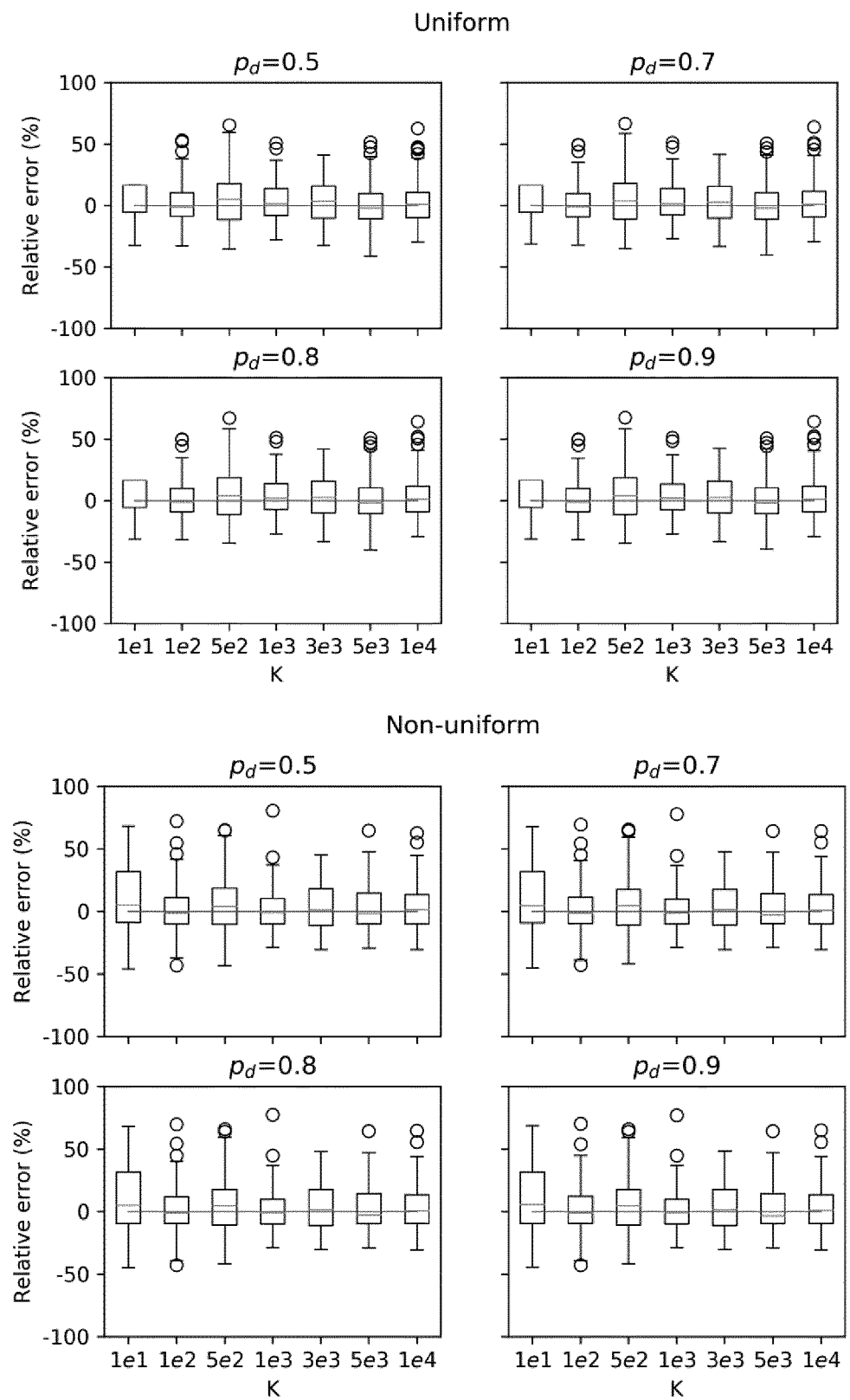

FIG. 10: Accuracy of Poisson-Normal method. Data from Poisson model with B=64 UMIs. Type of UMI distribution (uniform/non-uniform) and efficiency $p_d$ are given in the title of the graphics. Relative error of estimated number of pre-duplication fragments K on y-axis, true number on x-axis.

Figure 11:
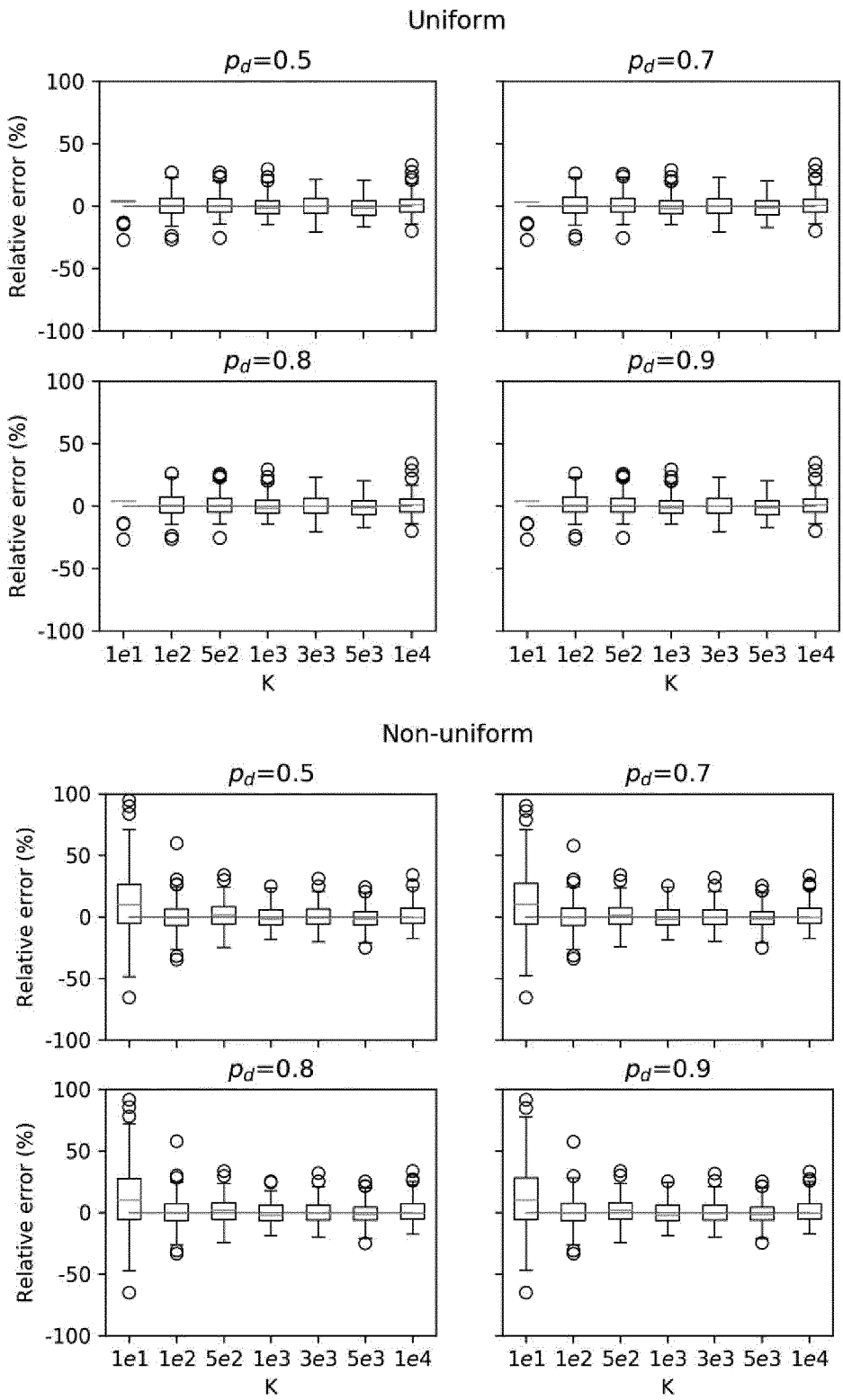

FIG. 11: Accuracy of Poisson-Normal method. Data from Poisson model with B=256 UMIs. Type of UMI distribution (uniform/non-uniform) and efficiency $p_d$ are given in the title of the graphics. Relative error of estimated number of pre-duplication fragments K on y-axis, true number on x-axis.

Figure 12:
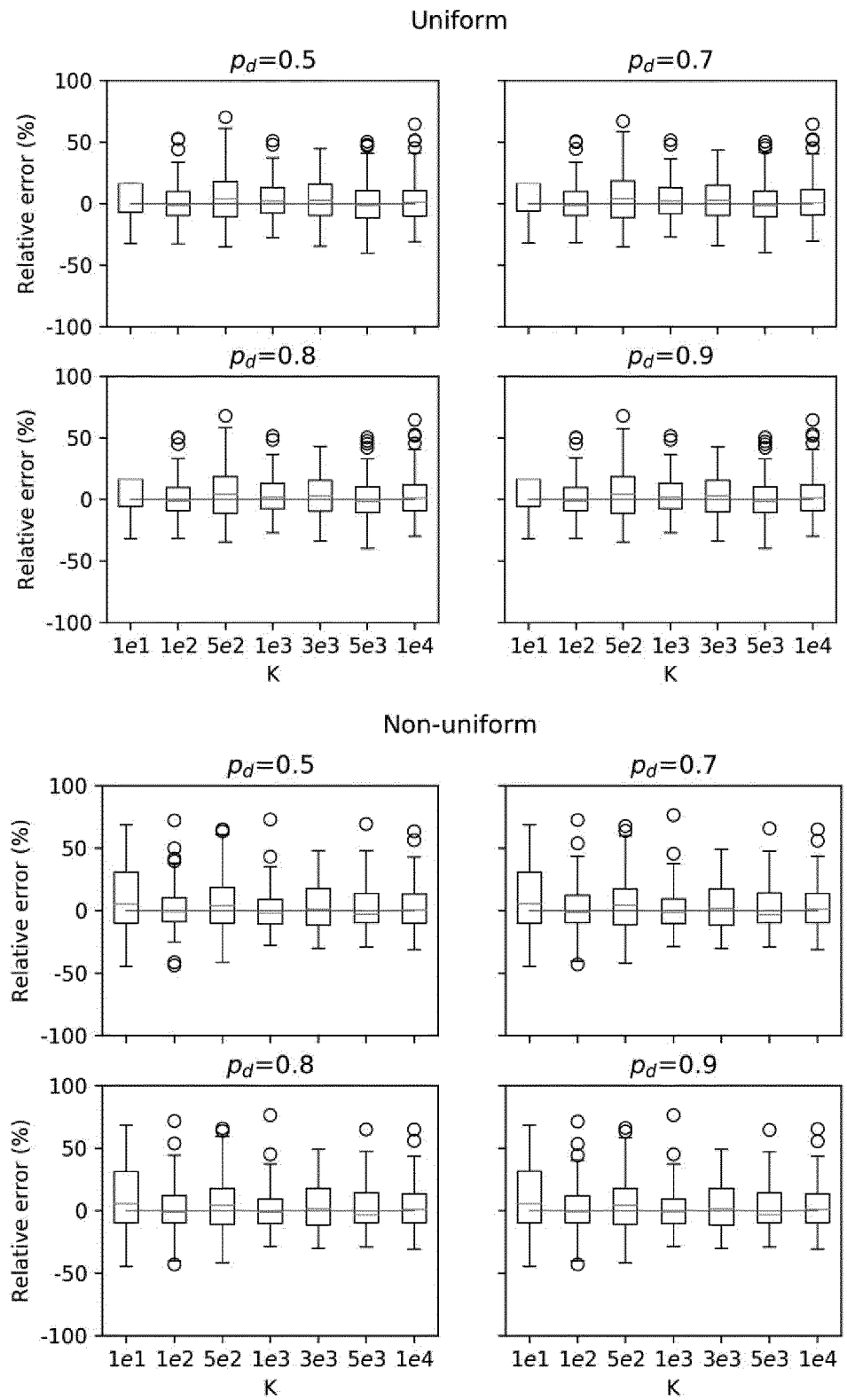

FIG. 12: Accuracy of Binomial-Normal method. Data from Binomial model with B=64 UMIs. Type of UMI distribution (uniform/non-uniform) and efficiency $p_d$ are given in the title of the graphics. Relative error of estimated number of pre-duplication fragments K on y-axis, true number on x-axis.

Figure 13:
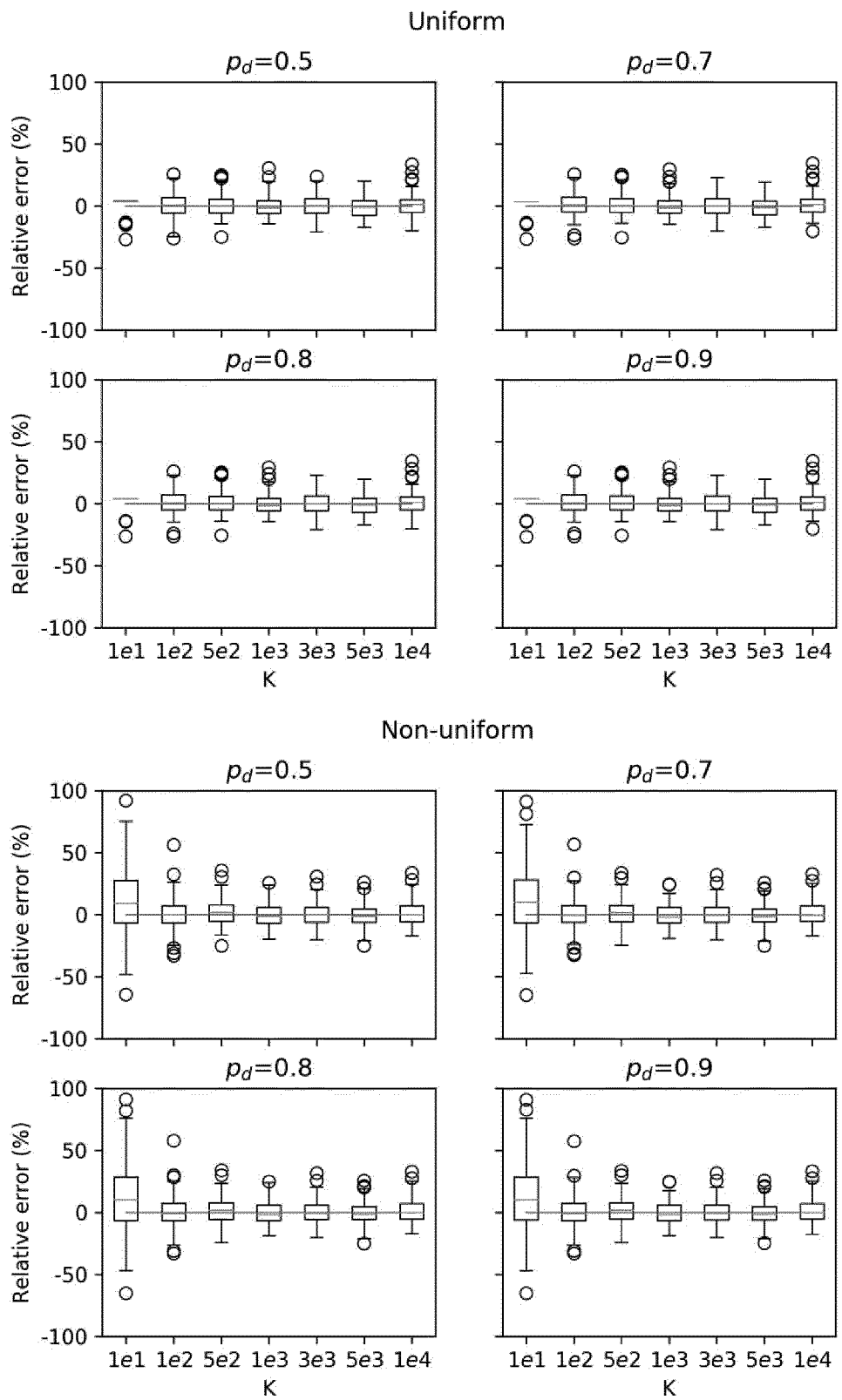

FIG. 13: Accuracy of Binomial-Normal method. Data from Binomial model with B=256 UMIs. Type of UMI distribution (uniform/non-uniform) and efficiency $p_d$ are given in the title of the graphics. Relative error of estimated number of pre-duplication fragments K on y-axis, true number on x-axis.

Figure 14:
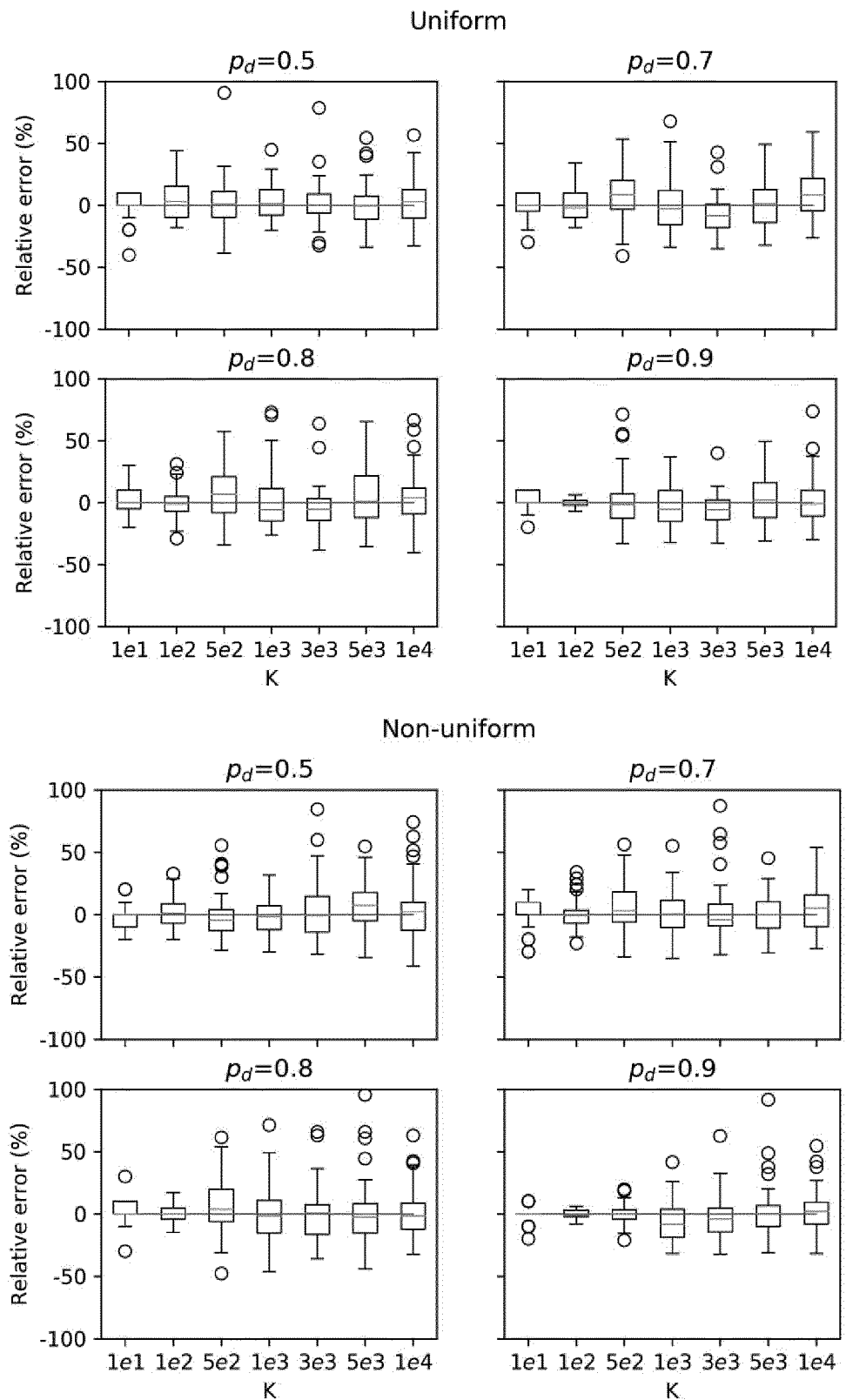

FIG. 14: Accuracy of GW multi-component mixture. Data from Galton-Watson model with B=64 UMIs. Type of UMI distribution (uniform/non-uniform) and efficiency $p_d$ are given in the title of the graphics. Relative error of estimated number of pre-duplication fragments K on y-axis, true number on x-axis.

Figure 15:
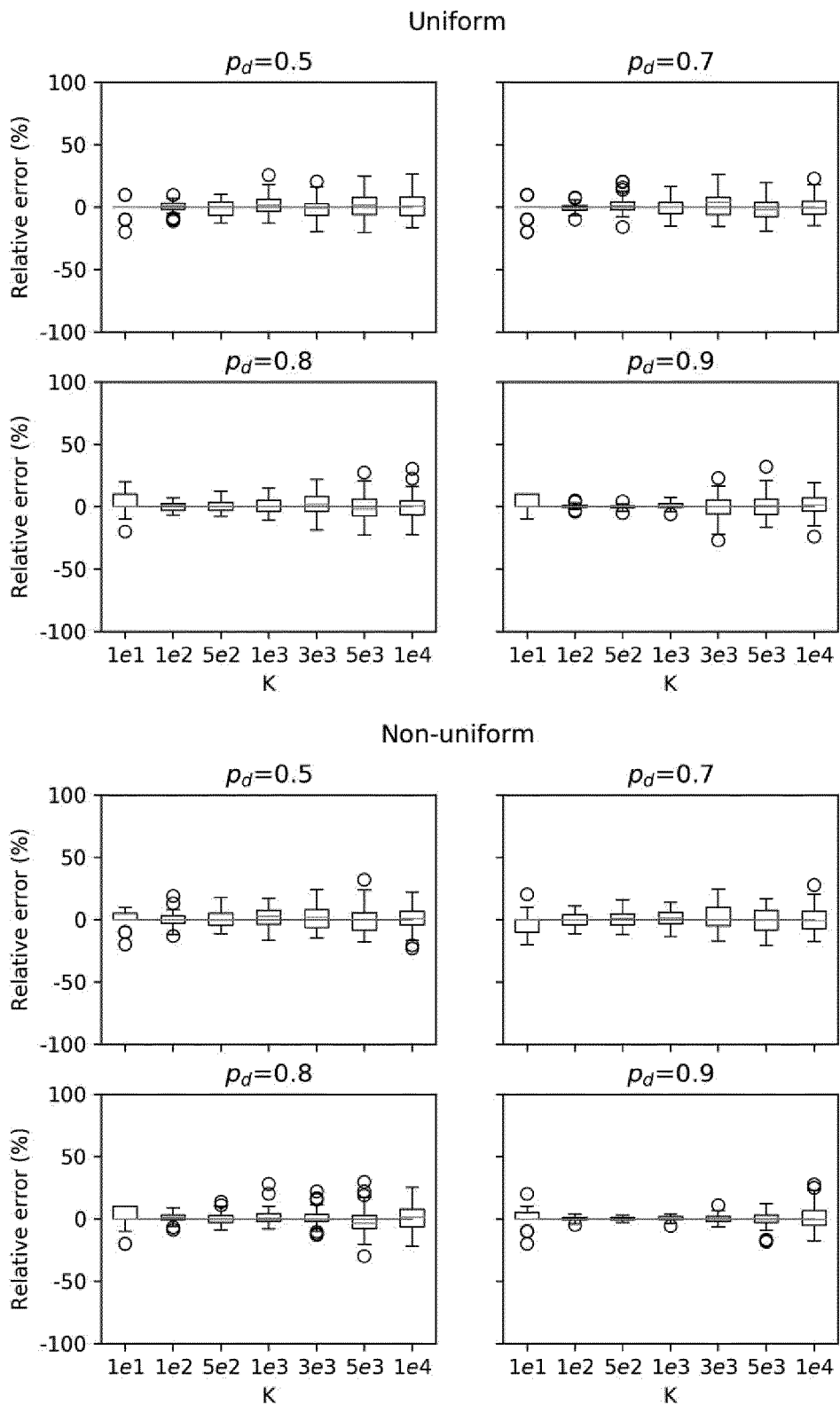

FIG. 15: Accuracy of GW multi-component mixture. Data from Galton-Watson model with B=256 UMIs. Type of UMI distribution (uniform/non-uniform) and efficiency $p_d$ are given in the title of the graphics. Relative error of estimated number of pre-duplication fragments K on y-axis, true number on x-axis.

EXAMPLE METHODS

The methods in this section for estimating pre-PCR numbers of fragment copies fall into two categories. The first, in Section 2.1, is based on the number of distinct observed UMIs. Since this is the same before and after PCR these methods are independent of the PCR process. Methods in the second category, in Section 2.2, are based on UMI counts after PCR. Since the latter are influenced by PCR these methods rely on statistical models for the PCR process. The methods in Section 2.1 and 2.2 require knowledge of the UMI distribution before PCR. This can be derived from the specification by which nucleotides were inserted at each position of the UMI or from the data available after PCR. Since the UMI distribution before PCR is not only affected by the frequency of nucleotide insertion but also the ligation bias, the second approach seems preferable. The corresponding methods are discussed in Section 2.3.

1. Preliminaries

In the following, we denote the total number of UMIs by B and the UMI labels by $b=1, \ldots, B$. The pre-PCR probability of UMI b will be denoted by $p_b$ and the complete UMI distribution before PCR by $\vec{p}=(p_1, \ldots, p_B)$. We further denote the total number of pools by F and the pool labels by $f=1, \ldots, F$. The number of pre-PCR counts of UMI b in pool f will be denoted by $k_b$ and the complete set of pre-PCR counts for all UMIs in pool f as $\vec{k}=(k_1, \ldots, k_B)$. Likewise, we denote the number of post-PCR counts of UMI b in pool f by $n_b$ and the complete set of post-PCR counts for all UMIs by $\vec{n} = (n_1, \ldots, n_B)$.

We further set $K = \Sigma_{i=1}^{B} k_b$ and $N = \Sigma_{i=1}^{B} n_b$.

Hence, K and N are the size of pool f before and after PCR. Note that we do not distinguish between different pools in our notation of pre- and post-PCR counts. It will always be understood in the following that methods are applied to a single pool unless explicitly stated otherwise.

2.1 Estimates from Number of Distinct Observed UMIs

2.1.1 Counting Distinct Observed UMIs

The simplest and most widely used method for inferring the pre-PCR number of fragment copies K from a post-PCR set of UMI counts $\vec{n}$ is to count the distinct UMIs observed in $\vec{n}$. This number will be denoted by $DU(\vec{n})$. The estimate of K is then given by $$K_{est} = DU(\vec{n}) = |\{i : n_i > 0\}| \tag{1}$$

This method produces sensible estimates only if ligating the same UMI to two different fragment copies is highly unlikely. This requires that B far outnumbers K and that the UMIs are evenly distributed. If K is large enough so that $DU(\vec{n})$ approaches B then (1) will underestimate the true K by a large margin.

2.1.2 Frequency Corrected Counting of Distinct Observed UMIs

Instead of simply counting the number of distinct observed UMIs it is more sensible to estimate K via the expected number of distinct elements drawn from a multinomial distribution with pre-duplication UMI distribution $\vec{p}$. This method will be referred to as frequency corrected UMI counting. If DU denotes the random variable of the number of distinct UMIs then $$E(DU \mid K, \vec{p}) = \sum_{b=1}^{B} (1 - (1 - p_b)^K) \tag{2}$$

The above formula is also given in [1] and [2] for uniformly distributed UMIs where it is used to estimate the deviation of UMI counting from the true number of pre-PCR fragment copies. Here we use (2) to estimate K by requesting that $$DU(\vec{n}) = E(DU \mid K_{est}, \vec{p}) \tag{3}$$

Equation (3) has, for general $\vec{p}$, no closed form solution but can be iteratively solved as follows $$K_0 = DU(\vec{n}) \tag{4}$$

$$K_{i+1} = \frac{K_i}{E(DU \mid K_i, \vec{p})} DU(\vec{n}) \tag{5}$$

This iterative procedure converges to the fixed point of (5) which solves (3). Hence, $K_i$ converges to the $K_{est}$ in (3). As before, this method requires N to be sufficiently small so that $DU(\vec{n})$ does not approaches B. In the extreme case where $DU(\vec{n}) = B$ this method will not converge.

2.2 Estimates from UMI Counts

In comparison to the previous section, the following methods make use of the full vector $\vec{n}$ of UMI counts after PCR. Since $\vec{n}$ is affected by duplication these methods require computational models for PCR. We factorize the probability of UMIs occurring $\vec{k}$ times before PCR and $\vec{n}$ times after PCR as follows $$p(\vec{n}, \vec{k} \mid K, \vec{p}, p_d) = p(\vec{k} \mid K, \vec{p}) p(\vec{n} \mid \vec{k}, p_d) \tag{6}$$

Here, $p(\vec{n} \mid \vec{k}, p_d)$ is the duplication model with duplication efficiency $p_d$. The latter will, in some cases, also be referred to as $\lambda$. It is further assumed that $\vec{k}$ is distributed multinomially with B outcomes, outcome probability $\vec{p}$ and K trials, i.e.

$$p(\vec{k} \mid K, \vec{p}) = \binom{K}{k_1, \ldots, k_B} \prod_{i=1}^{B} p_i^{k_i} \tag{7}$$

We develop three duplication models in this section. Poisson and Binomial models produce a single generation of offspring while the Galton-Watson process models multiple generations. The latter is a more accurate description of the PCR process and the corresponding methods should therefore yield better results on real data. The original number of fragment copies K and the efficiency $p_d$ can, in principle, be estimated by maximizing the probability $$p(\vec{n} \mid K, \vec{p}, p_d) = \sum_{\vec{k} : k_1 + \ldots + k_B = K} p(\vec{n}, \vec{k} \mid K, \vec{p}, p_d) \tag{8}$$

However, the number of summands in (8) becomes prohibitive for larger values of K. Instead, we estimate K and $p_d$ by maximizing either $$\prod_{b=1,\ldots,B} p(n_b \mid K, p_b, 1 - p_b, p_d) \text{ or} \tag{9}$$

$$\prod_{b=1,\ldots,B} p(n_b \mid N, K, p_b, 1 - p_b, p_d) \tag{10}$$

Here, $p(n_b \mid K, p_b, 1-p_b, p_d)$ is the probability of observing UMI b, $n_b$ times after PCR when the set of UMIs consists only of b and another UMI $\bar{b}$ with probabilities $p_b$ and $1-p_b$. The conditional probabilities in (10) depend, further, on N. Thus, equations (9) and (10) replace $p(\vec{n} \mid K, \vec{p}, p_d)$ with the product of B independent probability distributions each modeling post-PCR UMI counts for a dual UMI set. For notational convenience we drop $1-p_b$ from the probabilities in (9) and (10) and set $q_b = 1 - p_b$ in the following.

2.2.1 Poisson Duplication

For the Poisson model the probability of generating n from k fragments with a duplication efficiency $\lambda$ is given by the following Poisson probability $$p(n \mid k, \lambda) = P_{k\lambda}(n - k) \tag{11}$$

It can be shown that, in this case, the conditional probabilities $p(n \mid N, K, p_b, \lambda)$ in (10) have mean $\mu(N, K, p_b, \lambda)$ and variance $\sigma^2(N, K, p_b, \lambda)$ given by $$\mu(N, K, p_b, \lambda) = p_b N \quad \text{and} \tag{12}$$

$$\sigma^2(N, K, p_b, \lambda) = \left(N - K + 1 + \frac{N(N-1)}{K}\right) p_b q_b \tag{13}$$

Since (12) and (13) are independent of the efficiency λ, this parameter will be dropped from the notation in the following. For each UMI b, we use (12) and (13) as the mean and variance of a normal distribution. The K maximizing (10) can then be found as the positive root of the following quadratic polynomial.

$$K^2 - K((N+1) - N^2 V) - N(N-1) = 0 \tag{14}$$

$$\text{where } V = \frac{1}{B} \sum_{b=1}^{B} \frac{\left(\frac{n_b}{N} - p_b\right)^2}{p_b q_b} \tag{15}$$

Due to its derivation and the modeling of $p(n|N, K, p_b)$ by a normal distribution, this method will be called Poisson-Normal or P-Normal. The P-Normal method is independent of the duplication rate λ and very fast since (14) and (15) can be calculated efficiently.

2.2.2 Binomial Duplication

The Poisson duplication in the previous section allows an infinite number of fragments to be generated from a single one. In practice, however, only a finite number of fragments can be generated. A sensible replacement for the Poisson model is, therefore, the Binomial model. For the latter, the duplication probability is given by $$p(n|k, M, p_d) = \binom{Mk}{n-k} p_d^{n-k} q_d^{(M+1)k-n} \tag{16}$$

where M is the maximal number of fragments which can be generated from a single one and $p_d$ is the success probability in a single attempt of duplicating a fragment. As before, we set $q_d = 1 - p_d$. If each fragment can be replicated once in each PCR cycle then after c cycles $$M = 2^c - 1 \tag{17}$$

Further, if $p_d(1)$ is the probability that a fragment is duplicated after one cycle then the success probability in (16) after c cycles, $p_d(c)$, is given by $$p_d(c) = \frac{(1 + p_d(1))^c - 1}{M} \tag{18}$$

With increasing M the probability (16) converges to (11) with $\lambda = M p_d$. Asymptotically, therefore, Poisson and Binomial duplication models are equivalent. As before, the mean of the probability $p(n|N, K, M, p_b, p_d)$ is given by (12). The variance $\sigma^2(N, K, M, p_b, p_d)$, on the other hand, is given by $$\frac{1}{MK - 1} (-K^2(M+1) + K(MN + M + 2N + 1) + N(MN - M - N - 2)) p_b q_b \tag{19}$$

The expression (19) is, again, independent of the efficiency $p_d$ and converges to (13) for M→∞. As before, the K maximizing (10) can be found as the root of a quadratic polynomial if (12) and (19) are used as the mean and variance of a normal distribution in (10). In this case, the polynomial is given by $$K^2(M+1) - K(M(N-V+1) + 2N-1) - (N(MN-M-N-2)+V) = 0 \tag{20}$$

with V, as previously, defined by (15). This method for estimating K will be called Binomial-Normal or B-Normal.

2.2.3 Galton-Watson Duplication

The iterative nature of PCR is more appropriately modeled by a branching process than by Poisson or Binomial duplication models. Here, we choose a Galton-Watson process. The methods developed in this section will therefore be prefixed by Galton-Watson or GW. The offspring distribution is given by $p(2|1) = p_d$ and $p(1|1) = 1 - p_d$. Hence, in this model each fragment can spawn new offspring during a cycle with probability $p_d$. If k fragments are seen at the beginning of a cycle the probability that n fragments are seen at the end of the cycle is a binomial distribution, i.e.

$$p(n|k, p_d) = \binom{k}{n-k} p_d^{n-k} q_d^{2k-n} \tag{21}$$

If the number of cycles c is greater than one the probability $p(n|k, p_d, c)$ is best described via its probability generating function $PGF(p(n|k, p_d, c))(x)$, also called ordinary generating function. We have, see for instance Chapter 10 of [3], $$PGF(p(n|1, p_d, 1))(x) = q_d x + p_d x^2 \tag{22}$$

and $$PGF(p(n|k, p_d, c))(x) = (PGF(p(n|1, p_d, 1))^{\circ c})^k(x) \tag{23}$$

where $f^{\circ c}(x)$ is the c-fold composition and $f^k(x)$ the k-th power of function f(x). With this, one can write $$p(n|k, p_d, c) = \frac{1}{n!} \frac{d^n}{dx^n} PGF(p(n|k, p_d, c))(0) \tag{24}$$

In the following, we study uni- and multimodal distributions as models for $p(n|K, p_b, p_d, c)$ and make use of the fact that $$p(n|K, p_b, p_d, c) = \sum_{k=1}^{K} p(k|K, p_b) p(n|k, p_d, c) \tag{25}$$

$$p(k|K, p_b) = \binom{K}{k} p_b^k q_b^{K-k} \tag{26}$$

In order to simplify the search for a K maximizing (9) we, further, require that $p_d$ satisfies $$K = \frac{N}{(1 + p_d)^c} \tag{27}$$

Unimodal Distributions.

It can be shown that the mean and variance of the Galton-Watson duplication model in (25) with (24) are given by $$\mu(K, p_b, p_d, c) = (1 + p_d)^c p_b K \quad (28)$$

$$\sigma^2(K, p_b, p_d, c) = K p_b (1 + p_d)^c \left( (1 + p_d)^c \left( \frac{q_d}{1 + p_d} + q_b \right) - \frac{q_d}{1 + p_d} \right) \quad (29)$$

We define unimodal models for the Galton-Watson duplication process by setting the mean and variance of parametric distributions to (28) and (29). In our experiments we used the normal, Gamma and negative binomial distribution whose parameterization with respect to mean and variance are given, respectively, by $$f(x | \mu, \sigma^2) = \frac{1}{\sqrt{2\pi\sigma^2}} e^{\frac{(x-\mu)^2}{2\sigma^2}} \quad (30)$$

$$f(x | \mu, \sigma^2) = \frac{\beta^\alpha}{\Gamma(\alpha)} x^{\alpha-1} e^{-\beta x} \text{ with } \alpha = \frac{\mu^2}{\sigma^2}, \beta = \frac{\mu}{\sigma^2} \quad (31)$$

$$f(k | \mu, \sigma^2) = \binom{k+r-1}{k} (1-p)^r p^k \text{ with } p = \frac{\sigma^2 - \mu}{\sigma^2}, r = \frac{\mu^2}{\sigma^2 - \mu} \quad (32)$$

Multimodal Distributions.

Our experiments with the models in the last section showed that the distribution of the Galton-Watson duplication model is not appropriately described by a single mode. In this section we, therefore, model each component of the mixture in (25) separately. We make use of the fact that the probability of seeing b after PCR n times given that it was seen k times before has the following mean and variance $$\mu(k, p_d, c) = (1 + p_d)^c k \quad (33)$$

and $$\sigma^2(k, p_d, c) = q_d k (1 + p_d)^{c-1} ((1 + p_d)_c - 1) \quad (34)$$

Mixture of Delta and Unimodal Distribution.

Equations (33) and (34) show that for k=0 the distribution p(n|k, $p_d$, c) equals the Kronecker delta $\delta_0$. Hence, p(n|K, $p_d$, c) has a pronounced peak at n=0 for small K. Rather than modeling p(n|K, $p_d$, c) with a single distribution it is therefore sensible to model the two cases n=0 and n>0 separately. This can be done by writing p(n|K, $p_b$, $p_d$, c) as the mixture $$p(n|K, p_b, p_d, c) = p(n=0|K, p_b, p_d, c)\delta_0 + p(n>0|K, p_b, p_d, c) p(n|K, p_b, p_d, c, n>0) \quad (35)$$

For a mixture consisting of two components with weights $w_1$, $w_2$, means $\mu_1$, $\mu_2$ and standard deviations $\sigma_1$, $\sigma_2$ we have, according to the formulas for the overall mean $\mu$ and standard deviation $\sigma$ of the mixture $$\mu_2 = \frac{\mu - w_1 \mu_1}{w_2} \quad (36)$$

$$\sigma_2^2 = \frac{\sigma^2 - w_1((\mu_1 - \mu)^2 + \sigma_1^2)}{w_2} - (\mu_2 - \mu)^2 \quad (37)$$

Hence, $\mu_2$, $\sigma_2$ can be derived from $\mu$, $\sigma$, $\mu_1$, $\sigma_1$. If the first component corresponds to n=0 and the second to n≠0 then $w_1$ is given by $$p(n=0|K, p_b) = p(k=0|K, p_b) = (1-p_b)^K \quad (38)$$

Since $\mu_1$ and $\sigma_1$ are given by $\mu(\delta_0) = \sigma^2(\delta_0) = 0$ we have for $\mu_2$ $$\mu(K, p_b, p_d, c, n > 0) = \frac{\mu(K, p_b, p_d, c)}{p(n > 0 | K)} \quad (39)$$

and for $\sigma_2^2$ $$\sigma^2(K, p_b, p_d, c, n > 0) = \frac{p(n > 0 | K)\sigma^2(K, p_b, p_d, c) - p(n = 0 | K)\mu(K, p_b, p_d, c)^2}{p(n > 0 | K)^2} \quad (40)$$

As before, we can approximate p(n|K, $p_b$, $p_d$, c, n>0) with a parametric probability distribution by setting its mean and variance to (39) and (40). We, again, used the normal (30), Gamma (31) and negative binomial (32) distribution for this purpose.

Multi-component mixture. Even though mixtures of delta and unimodal distribution correctly describe the situation for small and large K we discovered a systematic bias for medium range K in our experiments. This is due to the fact that in this range the sum (25) is dominated by terms with small k for which approximation of p(n|k, $p_d$, c) by negative binomial or Gamma distribution is inaccurate. This can be seen in FIG. 6 which also show that the inaccuracy of approximation increases with increasing efficiency $p_d$. In fact, for $p_d$ close to 1 these figures exhibit a fractal-like structure where the overall shape is repeated at smaller scales.

In order to accommodate the complicated structure of mixture components in (25) we investigated an alternative model where p(n|K, $p_b$, $p_d$, c) is a mixture of more than two distributions whose means and variances are given by (33) and (34). For k=0 we again use the Kronecker delta $\delta_0$. For k>0 we initially fitted negative binomial distributions. However, we found that this gives a bad fit for small k. We therefore resorted to splitting the k's into a range of small, medium and large values. For small values we calculate p(n|k, $p_d$, c) exactly for each k with the help of (24), for medium values we use for each k a normal distribution with mean and variance given by (33) and (34), and we use a single negative binomial distribution for the partial sum of large k. We chose fixed boundaries for the ranges of k. In principle, however, these boundaries can be chosen adaptively to minimize the error between model and true distribution. In our experiments, small k ranged from k=0 to k=15, medium k ranged from k=16 to k=49 and large k were in the range starting at k=50.

Truncating Probability Distributions.

It should be noted that if p(n|k, $p_d$, c) is modeled by a distribution f(n) with f(n)>0 for n<k then f(n) has to be restricted to the range n≥k. This means that $$p(n | k, p_d, c) = \frac{f(n | K, d)}{1 - cdf_f(n-1)} \quad (41)$$

where $cdf_f(n)$ is the cumulative function of f(n). This, of course, also means that the mean and variance of p(n|k, $p_d$, c) do not coincide with those of the unrestricted f(n). In general, if a distribution pdf(n) is given by the restriction of another distribution f(n) to the range n≥k, then pdf(n)=cf(n) with c=1/(1−$cdf_f$(k−1)) and the mean and variance of the unrestricted f(n) have to equal $$\frac{1}{c}\mu(pdf) + \sum_{n=-\infty}^{k-1} f(n)n \text{ and} \quad (42)$$

$$\frac{1}{c}\sigma^2(pdf) - (\mu(pdf) - \mu(f))^2 + \sum_{n=-\infty}^{k-1} f(n)(\mu(pdf) - n)^2 dx \quad (43)$$

Calculating (42) and (43) is easy if f(n) is defined on non-negative integers, such as for a negative binomial or Gamma distribution. However, we found that truncation plays a minor role and use it only in the multi-component mixtures for the single negative binomial distribution for large k.

2.3 Estimating UMI Frequencies from the Data

Since (12) holds for Poisson, Binomial and Galton-Watson duplication models this shows that for data generated from these models $p_b$ can be estimated from the distribution of $n_b$. Rewriting (12) as follows $$E\left(\frac{n_b}{N} \mid N, K\right) = p_b \quad (44)$$

shows that the expected value of $$\frac{n_b}{N}$$

is independent of N and K. One strategy to estimate $p_b$ is therefore to calculate the mean of $$\frac{n_b}{N}$$

over all pools or identical fragments, F, i.e.

$$p_{b\_est} = \frac{1}{F}\sum_{f=1}^{F} \frac{n_{f,p}}{N_f} \quad (45)$$

This yields a probability distribution over b. Even though, the expected value in (44) is independent of N and K, the variance of $$\frac{n_b}{N}$$

is not. In order avoid the presence of outliers it can therefore make sense to calculate the mean of $$\frac{n_b}{N}$$

over a sufficiently large set of similarly sized N. Another alternative is to estimate $p_b$ by $$p_{b\_est} = \frac{\sum_{f=1}^{F} n_{f,b}}{\sum_{f=1}^{F} n_f} \quad (46)$$

This reduces the influence of small pools on the estimate of $p_b$.

3 Experiments

3.1 Generation of Synthetic Data

For our experiments we used B=64 and B=256 UMIs which were uniformly and non-uniformly distributed. For the non-uniform data the distribution of nucleotides at each position of the UMI was sampled from a Dirichlet distribution, i.e. from $$f((p_A, p_C, p_G, p_T); \alpha) = \frac{\Gamma(4\alpha)}{\Gamma(\alpha)^4}(p_A p_C p_G p_T)^{\alpha-1} \quad (47)$$

where $p_A$, $p_C$, $p_G$, $p_T$ are the probabilities of observing nucleotides A,C,G and T. Overall, the probability of UMI b is given by $$p_b = \prod_i p_{nt(b,i)} \quad (48)$$

where nt(b,i) is the nucleotide at the i-th position of barcode b and the product extends over all positions of b. We set $\alpha$=5 in (47). The corresponding probability density functions of $p_b$ for B=64 and B=256 are given in FIG. 7. This shows the variability of $p_b$ around 1/B (vertical line) and the asymmetric shape of their probability density function. Hence the sampled UMI distributions $\vec{p}$ are reasonably far from the uniform distribution. We tested our methods for K between 10 and 10000. For each K we sampled $\vec{p}$ between 50 and 100 times and for each sample $\vec{p}$ we drew $\vec{k}$ according to the multinomial distribution (7). Subsequently, we sampled $\vec{n}$ from the duplication model $p(\vec{n}|\vec{k})$ in (6) which is given for Poisson duplication by (11), for Binomial duplication by (16) and for Galton-Watson duplication by (24). We set the efficiency, $p_{d\_GW}$, in the Galton-Watson model to 0.5, 0.7, 0.8 and 0.9 and set the number of cycles to 15. For the Poisson and Binomial model, $\lambda$ and $p_{d\_Bin}$ are derived from $p_{d\_GW}$ by $$\lambda = (1 + p_{d\_GW})^c \quad (49)$$

$$p_{d\_Bin} = \frac{(1 + p_{d\_GW})^c - 1}{M} \quad (50)$$

where $M=2^c-1$. In the following, we refer to $p_{d\_Gw}$ rather than $\lambda$ and $p_{d\_Bin}$ and denote $p_{d\_GW}$ simply by $p_d$.

3.2 Results

The results for UMI counting for B=64 and B=256 UMIs can be found in FIG. 8, those for frequency corrected UMI counting are given in FIG. 9. In comparison to the other methods, both versions of UMI counting are independent of the duplication model and therefore of the duplication efficiency. For this reason we only include results for the Binomial duplication model with efficiency 0.5. Results for other duplication models and efficiencies are identical. FIG. 8 shows that UMI counting yields good estimates for K only if the number of UMIs, B, is considerably larger than K. For B=64 estimates are only reasonably accurate for K=10. For B=256 estimates for K=100 are also sensible. For larger values of K, however, UMI counting underestimates K by at least 50%. FIG. 8 further shows that UMI counting yields slightly less accurate results for non-uniform data. Frequency corrected counting in FIG. 9, on the other hand, produces more accurate results which are bias free for a wider range of K. However, for large K were the number of distinct observed UMIs, $DU(\vec{n})$, approaches B this method fails to converge or strongly overestimates K. A non-uniform barcode distribution extends the range in which the method converges. This is due to the fact that for an uneven barcode distribution it is more difficult to observe all UMIs and hence $DU(\vec{n})$ approaches B only for higher values of K. On the other hand, a non-uniform UMI distribution leads to a loss in accuracy for small values of K.

Results for the Poisson-Normal method, defined as the positive root of the quadratic equation in (14) and (15), are given for B=64 and B=256 in FIGS. 10 and 11. These results show that the accuracy of the P-Normal method is largely independent of the efficiency $p_d$. Non-uniformity, however, seems to have a negative effect on small K. In comparison to frequency corrected counting, P-Normal yields good results over the full range of K. FIGS. 12 and 13 give the results for the Binomial-Normal method. This shows that there is very little difference between the Poisson-Normal and Binomial-Normal method. As mentioned in Section 2.2.2, this is due the asymptotic equivalence of Poisson and Binomial duplication models. Minor differences between Poisson-Normal and Binomial-Normal methods can only be observed for small K.

FIGS. 14 and 15 contain the results for the GW-Multimix method which had the highest accuracy among all GW methods. FIGS. 14 and 15 show that accuracy increases slightly with increasing efficiency $p_d$. Non-uniformity, on the other hand, has little effect on the results. The GW-Multimix method produces valid results on the full range of K and is more accurate than Poisson-Normal and Binomial-Normal especially for small K. With B=256 UMIs and reasonably high efficiency accuracy of the GW-Multimix method far exceeds all other methods. Given the superiority of this method it might be worth modeling $p(n|N, K, p_b)$ with a multi-component mixture also for Poisson and Binomial duplication models.

In summary, our experiments show that our methods yield accurate estimates for the number of pre-duplication fragments K. These estimates are largely independent of the duplication efficiency $p_d$ and the pre-duplication distribution of UMIs $\vec{p}$. Apart from the frequency corrected UMI counting, all our methods yield results for the full range of investigated pre-PCR fragment numbers K.

REFERENCES

[1] Glenn K. Fu, Jing Hu, Pei-Hua Wang, and Stephen P. A. Fodor. Counting individual DNA molecules by the stochastic attachment of diverse labels. *Proceedings of the National Academy of Sciences*, 108(22):9026-9031, 2011.

[2] Glenn K. Fu, Weihong Xu, Julie Wilhelmy, Michael N. Mindrinos, Ronald W. Davis, Wenzhong Xiao, and Stephen P. A. Fodor. Molecular indexing enables quantitative targeted rna sequencing and reveals poor efficiencies in standard library preparations. *Proceedings of the National Academy of Sciences*, 111(5):1891-1896, 2014.

[3] Charles M. Grinstead and Laurie J. Snell. *Grinstead and Snell's Introduction to Probability*. American Mathematical Society, version dated 4 Jul. 2006 edition, 2006.

[4] Donald E. Knuth. *The art of computer programming: Sorting and searching*. Addison-Wesley, Second Edition, Chapter 6, 1998.

The invention claimed is:

1. Method of estimating a nucleic acid copy number in a sample comprising the steps of
   a) providing a sample comprising nucleic acids of a to be determined number of copies;
   b) attaching variable nucleotidic labels to said nucleic acids;
   c) amplifying said nucleic acids with the labels with a nucleic acid duplication procedure;
   d) determining amounts of amplified nucleic acid copies with a label, each amount is determined for nucleic acid copies with a different label; and
   e) providing an estimation of the nucleic acid copy number in the sample of step a) based on the determined amounts of step d) by
   approximating a probability of the labels of attaching to a nucleic acid by for at least two, or at least four, or at least ten or more, different nucleic acid species in the sample: averaging the amounts of said label for different nucleic acid species after amplification; and iteratively or stepwise (A)
   refining an expected number of nucleic acid copies in the sample based on the number of distinct detected labels in step d) and the expectation of the number of different labels to attach to a nucleic acid according to the probability of the labels of attaching to a nucleic acid copy and a previous iteration or pre-set value of an expected number of nucleic acid copies in the sample or an estimated amplification efficiency;
   or
   (B)
   (i) modelling probability distributions of amounts of amplified nucleic acid copies with a given label based on the determined amounts of step d), the probability of the labels of attaching to a nucleic acid, an estimated amplification efficiency or expected number of nucleic acid copies in the sample, and based on the expected duplication of amplified nucleic acid copies with a label in a nucleic acid duplication procedure per duplication cycle depending on said estimated amplification efficiency,
   (ii) determining the likelihood of the determined amount of nucleic acid copies with the labels to occur according to the modelled probability distribution of nucleic acid copies with the labels,
   (iii) maximizing a likelihood of step (ii) by varying the estimated amplification efficiency or expected number of nucleic acid copies in the sample,
   (iv) providing the estimation of the number of nucleic acid copies in the sample according to said maximized model or according to the estimated amplification efficiency at the maximized model.

2. The method of claim 1, wherein in step A) a pre-set value for a first iteration of an expected number of nucleic acid copies in the sample, an estimated amplification efficiency is selected from the value of the number of different detected labels in step d) or by an integer ranging from 1 to the determined amounts of amplified nucleic acid copies.

3. The method of claim 1, wherein in step B) the expected duplication of amplified nucleic acid copies with a label is modelled in a Gaussian, negative binomial, Gamma, Dirac delta or Galton-Watson duplication probability function or a mixture thereof.

4. The method of claim 1 wherein probability of the labels of attaching to a nucleic acid is determined according to formula (12), formula (45) or formula (46); and/or
  estimated amplification efficiency or expected number of nucleic acid copies in the sample are used interchangeably by conversion according to formula (27); and/or
  in step A), probability distributions of amounts of amplified nucleic acid copies with a given label is determined according to formula (5), formulas (4) and (5); or
  in step B), probability distributions of amounts of amplified nucleic acid copies with a given label is determined according to formula (25).

5. The method of claim 1, wherein the efficiency of amplifying said nucleic acids with the labels in said nucleic acid duplication procedure is not 100%.

6. The method of claim 1 wherein at least 20, or at least 30, or at least 40, distinct labels are attached to the nucleic acids.

7. The method of claim 1, wherein the nucleic acids are DNA or RNA.

8. The method of claim 1, wherein the amplification method is PCR.

9. The method of claim 1, wherein the amplification is for at least 1, 2, 3, 4, 5, 6, 7, 8 or more duplication cycles.

10. The method of claim 1, wherein modelling comprises using a stochastic branching model.

11. The method of claim 1, wherein a further iteration is based on at least 2 preceding iterations and wherein an estimated amplification efficiency or expected number of nucleic acid copies in the sample of the further iteration is selected with intervals which comprise the likelihood of the determined amount of nucleic acid copies with the labels to occur according to the modelled probability distribution of nucleic acid copies with the labels within said intervals and wherein the highest likelihoods of the determined amount of nucleic acid copies with the labels to occur according to the modelled probability distribution of nucleic acid copies with the labels are borders of said intervals.

12. A computer program product comprising computer readable instructions for calculating an estimation of the amount of nucleic acid copies in a sample based on a determined amount after an amplification of nucleic acids with attached labels according the steps of:
  1) approximating a probability of the labels of attaching to a nucleic acid by for at least two, or at least four, or at least ten or more, different nucleic acid species in the sample:
  2) averaging the amounts of said label for different nucleic acid species after amplification and iteratively or stepwise:
  (A) refining an expected number of nucleic acid copies in the sample based on the number of distinct detected labels and the expectation of the number of different labels to attach to a nucleic acid, according to the probability of the labels of attaching to a nucleic acid copy and a previous iteration or pre-set value of an expected number of nucleic acid copies in the sample or an estimated amplification efficiency;
  or
  (B)
  (i) modelling probability distributions of amounts of amplified nucleic acid copies with a given label, the probability of the labels of attaching to a nucleic acid, an estimated amplification efficiency or expected number of nucleic acid copies in the sample, and based on the expected duplication of amplified nucleic acid copies with a label in a nucleic acid duplication procedure per duplication cycle depending on the estimated amplification efficiency;
  (ii) determining the likelihood of the determined amount of nucleic acid copies with the labels to occur according to the modelled probability distribution of nucleic acid copies with the labels;
  (iii) maximizing a likelihood of step (ii) by varying the estimated amplification efficiency or expected number of nucleic acid copies in the sample;
  (iv) providing the estimation of the number of nucleic acid copies in the sample according to said maximized model or according to the estimated amplification efficiency at the maximized model;
  wherein the sample comprising nucleic acids of a to-be-determined number of copies is processed by the steps of:
  a) attaching variable nucleotidic labels to said nucleic acids;
  b) amplifying said nucleic acids with the labels with a nucleic acid duplication procedure; and
  c) determining amounts of amplified nucleic acid copies with a label, each amount is determined for nucleic acid copies with a different label prior to using the determined amounts in the estimation steps 1) and 2).

13. The computer program product of claim 12 adapted for presenting or displaying the result of steps 1) and 2) on a readable medium.

14. The method of performing steps 1) and 2) as defined in claim 12 on a computer.

15. The method of claim 1 comprising presenting or displaying the result of step e) on a readable medium.

* * * * *